US011897920B2

(12) United States Patent
Wei et al.

(10) Patent No.: US 11,897,920 B2
(45) Date of Patent: Feb. 13, 2024

(54) TALE RVD SPECIFICALLY RECOGNIZING DNA BASE MODIFIED BY METHYLATION AND APPLICATION THEREOF

(71) Applicants: PEKING UNIVERSITY, Beijing (CN); EDIGENE INC., Beijing (CN)

(72) Inventors: Wensheng Wei, Beijing (CN); Chengqi Yi, Beijing (CN); Yuan Zhang, Beijing (CN); Shengjie Guo, Beijing (CN); Chenxu Zhu, Beijing (CN); Lulu Liu, Beijing (CN)

(73) Assignees: Peking University, Beijing (CN); Edigene Inc., Beijing (CN)

( * ) Notice: Subject to any disclaimer, the term of this patent is extended or adjusted under 35 U.S.C. 154(b) by 883 days.

(21) Appl. No.: 16/636,283

(22) PCT Filed: Aug. 4, 2017

(86) PCT No.: PCT/CN2017/095988
§ 371 (c)(1),
(2) Date: Feb. 3, 2020

(87) PCT Pub. No.: WO2019/024081
PCT Pub. Date: Feb. 7, 2019

(65) Prior Publication Data
US 2021/0054030 A1    Feb. 25, 2021

(51) Int. Cl.
*C07K 14/195* (2006.01)
*C12N 9/22* (2006.01)
*C12N 15/113* (2010.01)
*C12N 15/66* (2006.01)

(52) U.S. Cl.
CPC .............. *C07K 14/195* (2013.01); *C12N 9/22* (2013.01); *C12N 15/113* (2013.01); *C12N 15/66* (2013.01); *C07K 2319/00* (2013.01); *C07K 2319/80* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 8,697,359 | B1 | 4/2014 | Zhang | |
|---|---|---|---|---|
| 8,932,814 | B2 | 1/2015 | Cong | |
| 9,879,315 | B2* | 1/2018 | Summerer | C12Q 1/6827 |
| 10,113,167 | B2 | 10/2018 | Doudna et al. | |
| 10,301,614 | B2* | 5/2019 | Duchateau | C12N 15/85 |
| 2011/0145940 | A1 | 6/2011 | Voytas et al. | |
| 2014/0134740 | A1 | 5/2014 | Gregory | |
| 2014/0273226 | A1 | 9/2014 | Wu | |
| 2014/0273233 | A1 | 9/2014 | Chen et al. | |
| 2015/0037809 | A1 | 2/2015 | Duchateau et al. | |
| 2016/0138094 | A1 | 5/2016 | Summerer et al. | |
| 2016/0177278 | A1* | 6/2016 | Wolfe | C12N 9/22 435/199 |
| 2016/0272965 | A1 | 9/2016 | Zhang et al. | |
| 2017/0049909 | A1 | 2/2017 | Cullen et al. | |
| 2017/0198302 | A1 | 7/2017 | Feng et al. | |
| 2018/0119138 | A1 | 5/2018 | Bauer et al. | |
| 2020/0255866 | A1 | 8/2020 | Wei et al. | |
| 2021/0163936 | A1 | 6/2021 | Wei et al. | |
| 2022/0064633 | A1 | 3/2022 | Wei et al. | |
| 2022/0186210 | A1 | 6/2022 | Wei et al. | |

FOREIGN PATENT DOCUMENTS

| CN | 102770539 A | 11/2012 |
|---|---|---|
| CN | 103025344 A | 4/2013 |
| CN | 103668472 A | 3/2014 |
| CN | 104651399 A | 5/2015 |
| CN | 105316341 A | 2/2016 |
| CN | 106062197 A | 10/2016 |
| CN | 106232823 A | 12/2016 |
| CN | 106637421 A | 5/2017 |
| CN | 107090466 A | 8/2017 |
| CN | 107513538 A | 12/2017 |
| CN | 107849581 A | 3/2018 |
| EP | 3536796 A1 | 9/2019 |

(Continued)

OTHER PUBLICATIONS

Adamson, B. et al. (2012). "A Genome-Wide Homologous Recombination Screen Identifies the RNA-Binding Protein RBMX as a Component of the DNA-Damage Response," Nat Cell Biol. 14(3):318-328, 27 pages.
Anders, S. et al. (2010). "Differential Expression Analysis for Sequence Count Data," Genome Biol 11:R106, 12 pages.
Auer, T.O. et al. (2014). "CRISPR/Cas9 and TALEN-Mediated Knock-In Approaches in Zebrafish," Methods, 9 pages.
Ausubel, F. et al. (1987). Current Protocols in Molecular Biology, Greene Publishing and Wiley Interscience, New York, TOC, 7 pages.
Billon, P. et al. (Sep. 21, 2017). "CRISPR-Mediated Base Editing Enables Efficient Disruption of Eukaryotic Genes through Induction of STOP Codons," Mol Cell 67:1068-1079.
Black, D.L. (2003). Mechanisms of Alternative Pre-Messenger RNA Splicing. Annual Review of Biochemistry. 72:291-336, 64 pages.

(Continued)

*Primary Examiner* — Brent T Page
(74) *Attorney, Agent, or Firm* — Morrison & Foerster LLP

(57) ABSTRACT

RVDs with recognition preferences for 5mC, 5hmC and 6 mA and different binding properties to these epigenetic modifications are identified in this present invention. Methylation-dependent gene activation, efficient genome editing, targeted detection of 5hmC and other applications can be achieved by using these RVDs. The present invention therefore provides an isolated DNA binding polypeptide containing TALEs, a fusion protein, a polynucleotide, a vector comprising the polynucleotide and a host cell, and the use of the protein comprising TALE repeats domain in the preparation of a reagent for detecting a methylated base in a target sequence of a gene of interest, as well as a method for targeting and binding to a target sequence of a gene of interest in a cell.

4 Claims, 13 Drawing Sheets

Specification includes a Sequence Listing.

(56) References Cited

FOREIGN PATENT DOCUMENTS

| | | | |
|---|---|---|---|
| JP | 2013529083 A | 7/2013 | |
| JP | 2015510772 A | 4/2015 | |
| KR | 20160118987 A | 10/2016 | |
| WO | 2011146121 A1 | 11/2011 | |
| WO | WO-2013102290 A1 * | 7/2013 | ........... C12Q 1/6813 |
| WO | WO2013102290 A1 | 7/2013 | |
| WO | 2013176772 A1 | 11/2013 | |
| WO | 2014018423 A2 | 1/2014 | |
| WO | 2014065596 A1 | 5/2014 | |
| WO | 2014130955 A1 | 8/2014 | |
| WO | 2014144592 A2 | 9/2014 | |
| WO | 2014144761 A2 | 9/2014 | |
| WO | 2014204724 A1 | 12/2014 | |
| WO | 2014206568 A1 | 12/2014 | |
| WO | 2015040075 A1 | 3/2015 | |
| WO | 2016011080 A2 | 1/2016 | |
| WO | 2016028843 A2 | 2/2016 | |
| WO | 2016142719 A1 | 9/2016 | |
| WO | 2016182893 A1 | 11/2016 | |
| WO | 2016184989 A1 | 11/2016 | |
| WO | 2016205745 A2 | 12/2016 | |
| WO | 2017214460 A1 | 12/2017 | |
| WO | 2018154027 A1 | 8/2018 | |
| WO | 2019028686 A1 | 2/2019 | |
| WO | 2019191876 A1 | 10/2019 | |
| WO | 2020125762 A1 | 6/2020 | |
| WO | 2020192712 A1 | 10/2020 | |

OTHER PUBLICATIONS

Boch, J. et al. (2010, e-pub. May 10, 2010). "Xanthomonas AvrBs3 Family-Type III Effectors: Discovery and Function," Annu Rev Phytopathol 48:419-436.
Boch, J. et al. (Dec. 11, 2009). "Breaking the Code of DNA Binding Specificity of TAL-Type III Effectors," Science 326(5959):1509-1512.
Bogdanove, A.J. et al. (Sep. 30, 2011). "TAL Effectors: Customizable Proteins for DNA Targeting," Science 333(6051):1843-1846.
Bradley, K.A. et al. (Nov. 8, 2001). "Identification of the Cellular Receptor for Anthrax Toxin," Nature 414:225-229.
Bultmann, S. et al. (2012, e-pub. Mar. 2, 2012). "Targeted Transcriptional Activation of Silent oct4 Pluripotency Gene by Combining Designer TALEs and Inhibition of Epigenetic Modifiers," Nucleic Acids Res 40(12):5368-5377.
Burkard, M.E. et al. (Mar. 15, 2012). "Enabling and Disabling Polo-Like Kinase 1 Inhibition Through Chemical Genetics," ACS Chemical Biology 7:978-981.
Canver, M.C. et al. (2015). "BCL11A Enhancer Dissection by Cas9-Mediated In Situ Saturating Mutagenesis," Nature 527:192-197.
Chapman, J.R. et al. (Aug. 24, 2012). "Playing the End Game: DNA Double-Strand Break Repair Pathway Choice," Mol. Cell. 47:497-510.
Chen, B. et al. (Dec. 19, 2013). "Dynamic Imaging of Genomic Loci in Living Human Cells by an Optimized CRISPR/Cas System," Cell 155:1479-1491.
Chen, D. et al. (2011). "Bortezomib as the First Proteasome Inhibitor Anticancer Drug: Current Status and Future Perspectives," Curr. Cancer Drug Targets 11:239-253.
Chen, F. et al. (Sep. 2011, e-published on Jul. 17, 2011). "High-Frequency Genome Editing Using ssDNA Oligonucleotides With Zinc-Finger Nucleases," Nature Methods 8(9):753-755.
Christian, M. et al. (Oct. 2010, e-pub. Jul. 26, 2010). "Targeting DNA Double-Strand Breaks With TAL Effector Nucleases," Genetics 186(2):757-761.
Clancy, S. (2008). "RNA Splicing: Introns, Exons and Spliceosome," Nature Education 1:31, 3 pages.
Cong, L. et al. (2012). "Comprehensive Interrogation of Natural TALE DNA-Binding Modules and Transcriptional Repressor Domains," Nat Commun. 3:968, 14 pages.

Cong, L. et al. (Feb. 15, 2013). "Multiplex Genome Engineering Using CRISPR/Cas Systems," Science 339(6121):819-823, 9 pages.
Cristea, S. et al. (2013, e-pub. Oct. 5, 2012). "In vivo Cleavage of Transgene Donors Promotes Nuclease-Mediated Targeted Integration," Biotechnol. & Bioeng. 110(3):871-880.
Crooks, G. E. et al. (2004). "WebLogo: A Sequence Logo Generator," Genome Res. 14:1188-1190.
De Wilt, L.H.A.M et al. (2012, e-pub. Oct. 18, 2011). "Proteasome-Based Mechanisms of Intrinsic and acquired Bortezomib Resistance in Non-Small Cell Lung Cancer," Biochem. Pharmacol. 83:207-217.
Deng, D. et al. (2012). "Recognition of Methylated DNA by TAL Effectors," Cell research 22(10):1502-1504.
Deng, D. et al. (Feb. 10, 2012, e-pub. Jan. 5, 2012). "Structural Basis for Sequence-Specific Recognition of DNA by TAL Effectors," Science 335(6069):720-723, 9 pages.
Duan, J. et al. (2004). "Structural and Functional Analysis of Mutations at the Human Hypoxanthine Phosphoribosyl Transferase (HPRT1) Locus," Human Mutation 23:599-611.
Dupuy, A. et al. (Nov. 13, 2013). Targeted Gene Therapy of Xeroderma Pigmentosum Cells Using Meganuclease and Talen, PLoS One 8(11):e78678, 8 pages.
Engler, C. et al. (May 14, 2009). "Golden Gate Shuffling: A One-Pot DNA Shuffling Method Based on Type IIs Restriction Enzymes," PLoS One 4:e5553, 9 pages.
Engreitz, J.M. et al. (Nov. 17, 2016). "Local Regulation of Gene Expression by lncRNA Promoters, Transcription and Splicing," Nature 539(7629):452-455, with Supplemental, 19 pages.
Extended European Search Report, dated May 10, 2022, for European Patent Application No. 20777188.2, 10 pages.
Extended European Search Report, dated Oct. 20, 2021, for European Patent Application No. 18913494.3, 10 pages.
Ezkurdia, I. et al. (2014, e-pub. Jun. 16, 2014). "Multiple Evidence Strands Suggest That There May Be as Few as 19,000 Human Protein-Coding Genes," Hum. Mol. Genet. 23:5866-5878.
Fang, G. et al. (Dec. 2012). "Genome-Wide Mapping of Methylated Adenine Residues in Pathogenic *Escherichia coli* Using Single-Molecule Real-Time Sequencing," Nature biotechnology 30(12):1232-1239, 23 pages.
Findlay, G.M. et al. (2014). "Saturation Editing of Genomic Regions by Multiplex Homology-Directed Repair," Nature 513:120-123.
Franke, N.E. et al. (2012, e-pub. Sep. 23, 2011). "Impaired Bortezomib Binding to Mutant β5 Subunit of the Proteasome Is the Underlying Basis for Bortezomib Resistance in Leukemia Cells," Leukemia 26:757-768.
Freshney, R. I., (1987) "Culture of Specific Cell Types" Chapter 20 in Culture of Animal Cells: A Manual of Basic Techniques, Alan R. Liss & Co., New York; pp. 257-260, 270-273.
Fu, S. et al. (Jun. 18, 2010). "The Structure of Tumor Endothelial Marker 8 (TEM8) Extracellular Domain and Implications for Its Receptor Function for Recognizing Anthrax Toxin," PLoS One 5:e11203, 10 pages.
Fu, Y. et al. (May 7, 2015). "N6-Methyldeoxyadenosine Marks Active Transcription Start Sites in Chlamydomonas," Cell 161:1-14.
Fu, Y. et al. (Sep. 2013). "High-Frequency Off-Target Mutagenesis Induced by CRISPR-Cas Nucleases in Human Cells," Nat Biotechnol 31:822-826, 13 pages.
Garg, A. et al. (2012, e-pub. May 11, 2012). "Engineering Synthetic TAL Effectors With Orthogonal Target Sites," Nucleic Acids Res 40(15):7584-7595.
Garst, A.D. et al. (2017, e-pub. Dec. 12, 2016). "Genome-Wide Mapping of Mutations at Single-Nucleotide Resolution for Protein, Metabolic and Genome Engineering," Nat. Biotechnol. 35:48-55.
GenBank NR_110533.1, Shin, S.Y. et al. (Oct. 8, 2016). "*Homo sapiens* DiGeorge Syndrome Critical Region Gene 5 (Non-Protein Coding) (DGCR5). Transcript Variant 3, Non-Coding RNA," 2 pages.
Gilbert, L.A. et al. (Jul. 18, 2013). "CRISPR-Mediated Modular RNA-Guided Regulation of Transcription in Eukaryotes," Cell 154:442-451.

(56) References Cited

OTHER PUBLICATIONS

Gilbert, L.A. et al. (Oct. 23, 2014). "Genome-Scale CRISPR-Mediated Control of Gene Repression and Activation," Cell 159:647-661.
Goyal, A. et al. (2017, e-pub. Sep. 30, 2016). "Challenges of CRISPR/Cas9 Applications for Long Non-Coding RNA Genes," Nucleic Acids Res 45(3):e12, 13 pages.
Greer, E.L. et al. (May 7, 2015). "DNA Methylation on N6-Adenine in C. elegans," Cell 161:868-878, 26 pages.
Guttman, M. et al. (2011). "lincRNAs Act in the Circuitry Controlling Pluripotency and Differentiation," Nature 477(7364):295-300, 32 pages.
Gürlebeck, D. et al. (2006). "Type III Effector Proteins From the Plant Pathogen Xanthomonas and Their Role in the Interaction With the Host Plant," J Plant Physiol. 163(3):233-255.
Harlow, E. et al. (1988). Antibodies A Laboratory Manual, Table of Contents only, 9 pages.
Hart, T. et al. (2014). "Measuring Error Rates in Genomic Perturbation Screens: Gold Standards for Human Functional Genomics," Molecular Systems Biology 10:733, 16 pages.
Hart, T. et al. (Dec. 3, 2015). "High-Resolution CRISPR Screens Reveal Fitness Genes and Genotype-Specific Cancer Liabilities," Cell 163:1-12.
He, Y.-F. et al. (Sep. 2, 2011). "Tet-Mediated Formation of 5-Carboxylcytosine and Its Excision by TDG in Mammalian DNA," Science 333(6047):1303-1307, 10 pages.
Heckl, D. et al. (Sep. 30, 2014). "Generation of Mouse Models of Myeloid Malignancy With Combinatorial Genetic Lesions Using CRISPR-Cas9 Genome Editing," Nat. Biotechnol. 32(9):941-946, 14 pages.
Heidari, N. et al. (2014). "Genome-Wide Map of Regulatory Interactions in the Human Genome," Genome Res. 24:1905-1917.
Jess, G.T. et al. (2016, e-pub. Oct. 31, 2016). "Directed Evolution Using dCas9-Targeted Somatic Hypermutation in Mammalian Cells," Nat. Methods, 10 pages.
Hsu, P.D. et al. (Sep. 2013). "DNA Targeting Specificity of RNA-Guided Cas9 Nucleases," Nat Biotechnol. 31:827-832, 17 pages.
Hsu, PD. et al. (Jun. 5, 2014). "Development and Applications of CRISPR-Cas9 for Genome Engineering," Cell 157(6):1262-1278, 34 pages.
Hu, J. et al. (2014). "Direct Activation of Human and Mouse Oct4 Genes Using Engineered TALE and Cas9 Transcription Factors," Nucleic Acids Res 42(7):4375-4390, 19 pages.
Huang, Y. et al. (Oct. 2014). "Connections Between TET Proteins and Aberrant DNA Modification in Cancer," Trends Genet 30(10):464-474, 25 pages.
International Preliminary Report on Patentability Opinion, dated Jun. 16, 2021, for PCT Application No. PCT/CN2019/127080, filed Dec. 20, 2019, 4 pages.
International Preliminary Report on Patentability Opinion, dated Sep. 28, 2021, for PCT Application No. PCT/CN2020/081283, filed Mar. 26, 2022, 5 pages.
International Search Report and Written Opinion, dated Jul. 1, 2020, for PCT Application No. PCT/CN2020/081283, filed Mar. 26, 2022, 10 pages.
International Search Report and Written Opinion, dated Mar. 25, 2020, for PCT Application No. PCT/CN2019/127080, filed Dec. 20, 2019, 8 pages.
International Search Report, dated Jan. 4, 2019, for PCT Application No. PCT/CN2018/081635, 6 pages.
International Search Report, dated May 14, 2018, for PCT Application No. PCT/CN2017/096510, English Translation, 2 pages.
Ito, S. et al. (Aug. 26, 2010). "Role of Tet Proteins In 5mC to 5hmC Conversion, ES-Cell Self-Renewal and Inner Cell Mass Specification," Nature 466(7310):1129-1133.
Jackson, S.P. (2002). "Sensing and Repairing DNA Double-Strand Breaks," Carcinogenesis 23(5):687-696.
Jiao, X. et al. (2012). "DAVID-WS: A Stateful Web Service to Facilitate Gene/Protein List Analysis," Bioinformatics 28:1805-1806.

Jinek, M. et al. (Aug. 17, 2012, e-pub. Jun. 28, 2012). "A Programmable Dual-RNA-Guided DNA Endonuclease in Adaptive Bacterial Immunity," Science 337(6096):816-821, 14 pages.
Joung, J. et al. (Aug. 17, 2017). "Genome-Scale Activation Screen Identifies a LncRNA Locus Regulating a Gene Neighborhood," Nature 548(7667):343-346, 28 pages.
Kaufman, R.J. et al. (1987). "Translational Efficiency of Polycistronic mRNAs and Their Utilization to Express Heterologous Genes in Mammalian Cells," The EMBO Journal 6(1):187-195.
Kay, S. et al. (2009). "How Xanthomonas Type III Effectors Manipulate the Host Plant," Curr Opin Microbiol 12(1):37-43.
Kay, S. et al. (Oct. 26, 2007). "A Bacterial Effector Acts as a Plant Transcription Factor and Induces a Cell Size Regulator," Science 318(5850):648-651.
Kim, H. et al. (Nov. 2011). "Surrogate Reporters for Enrichment of Cells With Nuclease-Induced Mutations," Nat. Methods 8(11):941-943.
Kim, H.J. et al. (2009). "Targeted Genome Editing in Human Cells With Zinc Finger Nucleases Constructed via Modular Assembly," Genome Res. 19:1279-1288.
Kim, Y. et al. (Mar. 2013, e-pub. Feb. 17, 2013). "A Library of TAL effector Nucleases Spanning the Human Genome," Nat Biotechnol 31(3):251-258.
Kim, Y.-G. et al. (Feb. 1996). "Hybrid Restriction Enzymes: Zinc Finger Fusions to Fok I Cleavage Domain," Proc. Natl. Acad. Sci. USA 93:1156-1160.
Kohli, R.M. et al. (Oct. 24, 2013). TET Enzymes, TDG and the Dynamics of DNA Demethylation, Nature 502(7472):472-479, 21 pages.
Koike-Yusa, H. et al. (2014, e-pub. Dec. 23, 2013). "Genome-wide Recessive Genetic Screening in Mammalian Cells With a Lentiviral CRISPR-Guide RNA Library." Nat Biotechnol 32:267-273.
Kolde, R. et al. (2012, e-pub. Jan. 12, 2012). "Robust Rank Aggregation for Gene List Integration and Meta-Analysis," Bioinformatics 28(4):573-580.
Konermann, S. et al. (Jan. 29, 2015). "Genome-Scale Transcriptional Activation by an Engineered CRISPR-Cas9 Complex," Nature 517:583-588.
Koziol, M.J. et al. (Jan. 2016). "Identification of Methylated Deoxyadenosines in Vertebrates Reveals Diversity in DNA Modifications," Nature Structural & Molecular Biology 23(1):24-30, 23 pages.
Kretz, M. et al. (Jan. 10, 2013). "Control of Somatic Tissue Differentiation by the Long Non-Coding RNA TINCR," Nature 493:231-235, 16 pages.
Kriaucionis, S. et al. (Apr. 16, 2009). The Nuclear DNA Base 5-Hydroxymethylcytosine Is Present in Purkinje Neurons and the Brain, Science 324(5929):929-930.
Kubik, G. et al. (Jan. 5, 2015). "Programmable Sensors of 5-Hydroxymethylcytosine," J Am Chem Soc 137(1):2-5.
Kubik, G. et al. (2014). "Programmable and Highly Resolved In Vitro Detection of 5-Methylcytosine by TALEs," Angew Chem Int Ed Engl 53(23):6002-6006.
Kubik, G. et al. (2015). "Achieving Single-Nucleotide Resolution of 5-Methylcytosine Detection With TALEs," Chembiochem 16(2):228-231.
Lackner, D.H. et al. (Dec. 17, 2015). "A Generic Strategy for CRISPR-Cas9-Mediated Gene Tagging," Nature Communications 6:10237, 7 pages.
Leng, N. et al. (2013, e-pub. Feb. 21, 2013). "EBSeq: An Empirical Bayes Hierarchical Model for Inference in RNA-Seq Experiments," Bioinformatics 29(8):1035-1043.
Li, B. et al. (2011). "RSEM: Accurate Transcript Quantification From RNA-Seq Data With or Without a Reference Genome," BMC Bioinformatics 12:323, 16 pages.
Li, H.L. et al. (2016, e-pub. Oct. 23, 2015). "Efficient Genomic Correction Methods in Human iPS Cells Using CRISPR-Cas9 System," Methods 101:27-35.
Li, K. et al. (Aug. 28, 2014). "Optimization of Genome Engineering Approaches with the CRISPR/Cas9 System," PLoS One 9(8):e105779, 10 pages.

(56) References Cited

OTHER PUBLICATIONS

Li, W. et al. (2014). "MAGeCK Enables Robust Identification of Essential Genes From Genome-Scale CRISPR/Cas9 Knockout Screens," Genome Biol 15:554, 12 pages.

Liao, S. et al. (2015, e-pub. Jun. 29, 2015). "Enriching CRISPR-Cas9 Targeted Cells by Co-Targeting the HPRT Gene," Nucleic Acids Res. 43(20):e134, 8 pages.

Lim, K.H. et al. (Jul. 5, 2011). "Using Positional Distribution to Identify Splicing Elements and Predict Pre-mRNA Processing Defects in Human Genes," Proc. Natl. Acad. Sci. USA. 108(27):11093-11098.

Lin, N. et al. (Mar. 2014). "An Evolutionarily Conserved Long Noncoding RNA TUNA Controls Pluripotency and Neural Lineage Commitment," Mol. Cell. 53:1005-1019.

Liu, S.J. et al. (Jan. 6, 2017). "CRISPRi-Based Genome-Scale Identification of Functional Long Noncoding RNA Loci in Human Cells," Science 355(6320):1-19.

Liu, Y. et al. (Dec. 2018, e-pub. Nov. 5, 2018). "Genome-Wide Screening for Functional Long Noncoding RNAs in Human Cells by Cas9 Targeting of Splice Sites," Nature Biotechnology 36(12):1203-1210.

Long, C. et al. (Jan. 31, 2018). "Correction of Diverse Muscular Dystrophy Mutations in Human Engineered Heart Muscle by Single-Site Genome Editing," Science Advances 4:eaap9004, 11 pages.

Lyras, D. et al. (2009). "Toxin B Is Essential for Virulence of Clostridium difficile," Nature 458:1176-1179.

Lü, S. et al. (2013). "The Resistance Mechanisms of Proteasome Inhibitor Bortezomi," Biomarker Research 1:13, 9 pages.

Ma, H. et al. (Mar. 10, 2015). "Multicolor CRISPR Labeling of Chromosomal Loci in Human Cells," Proc. Natl. Acad. Sci. USA 112:3002-3007.

Maiti, A. et al. (Oct. 14, 2011). "Thymine DNA Glycosylase Can Rapidly Excise 5-Formylcytosine and 5-Carboxylcytosine: Potential Implications for Active Demethylation of CpG Sites," J Biol Chem 286(41):35334-35338.

Mak, A.N.-S. et al. (Feb. 10, 2012) "The Crystal Structure of TAL Effector PthXo1 Bound to Its DNA Target," Science 335(6069):716-719, 11 pages.

Mali, P. et al. (Feb. 15, 2013, e-pub. Jan. 3, 2013). "RNA Guided Human Genome Engineering via Cas9," Science 339(6121):823-826, 8 pages.

Matlin, A.J. et al. (May 2005). "Understanding Alternative Splicing: Towards a Cellular Code," Nat. Rev. Mol. Cell Biol. 6:386-398.

Maurer, S. et al. (Nov. 4, 2016). "Interrogating Key Positions of Size-Reduced TALE Repeats Reveals a Programmable Sensor of 5-Carboxylcytosine," ACS Chem Biol 11(12):3294-3299.

Meyers, R.M. et al. (2017, e-pub. Oct. 30, 2017). "Computational Correction of Copy Number Effect Improves Specificity of CRISPR-Cas9 Essentiality Screens in Cancer Cells," Nat Genet 49:1779-1784.

Michlits, G. et al. (2017, e-pub. Oct. 16, 2017). "CRISPR-UMI: Single-Cell Lineage Tracing of Pooled CRISPR-Cas9 Screens," Nat Methods 14:1191-1197.

Miller, J.C. et al. (Feb. 2011, e-pub. Dec. 22, 2010). "A TALE Nuclease Architecture for Efficient Genome Editing," Nature Biotechnology 29(2):143-148.

Miller, J.C. et al. (May 2015, e-pub. Mar. 23, 2015). "Improved Specificity of TALE-Based Genome Editing Using an Expanded RVD Repertoire," Nat Methods 12(5):465-471.

Mitamura, T. et al. (Oct. 24, 1997). "Structure-Function Analysis of the Diphtheria Toxin Receptor Binding Site by Site-Directed Mutagenesis," J. Biol. Chem. 272:27084-27090.

Miyaoka, Y. et al. (Mar. 2014). "Isolation of Single-Base Genome-Edited Human iPS Cells Without Antibiotic Selection," Nat Methods 11:291-293, 15 pages.

Morbitzer, R. (Dec. 14, 2010). "Regulation of Selected Genome Loci Using De Novo-Engineered Transcription Activator-Like Effector (TALE)-Type Transcription Factors," Proc Natl Acad Sci USA 107(50):21617-21622.

Moscou, M.J. et al. (Dec. 11, 2009, e-pub. Oct. 29, 2009). "A Simple Cipher Governs DNA Recognition by TAL Effectors," Science 326:1501, 1 page.

Muller, R.Y. et al. (2015). "An Efficient Method for Electroporation of Small Interfering RNAs into ENCODE Project Tier 1 GM12878 and K562 Cell Lines," J. Biomol. Tech 26:142-149.

Murugan, R.N. et al. (Sep. 30, 2011). "Plk1-Targeted Small Molecule Inhibitors: Molecular Basis for Their Potency and Specificity," Mol. Cells 32:209-220.

Mussolino, C. et al. (2011, e-pub. Aug. 3, 2011). "A Novel TALE Nuclease Scaffold Enables High Genome Editing Activity in Combination With Low Toxicity," Nucleic Acids Res 39(21):9283-9293.

Nakade, S. et al. (Nov. 20, 2014). "Microhomology-Mediated End-Joining-Dependent Integration of Donor DNA in Cells and Animals Using TALENs and CRISPR/Cas9," Nature Communications 5:5560, 8 pages.

Ng, B, et al. (Dec. 2004). "Increased Noncanonical Splicing of Autoantigen Transcripts Provides the Structural Basis for Expression of Untolerized Epitopes," Journal of Allergy and Clinical Immunology 114(6):1463-1470, 17 pages.

Nishimasu, H. et al. (Feb. 27, 2014). "Crystal Structure of cas9 in Complex With Guide RNA and Target DNA," Cell 156:935-949.

O'Brien, A. et al. (2014). "GT-Scan: Identifying Unique Genomic Targets," Bioinformatics 30(18):2673-2675.

Orlando, S.J. et al. (Aug. 2010, e-pub, Jun. 8, 2010). "Zinc-finger Nuclease-Driven Targeted Integration Into Mammalian Genomes Using Donors With Limited Chromosomal Homology," Nucleic Acids Research 38(15):e152, 15 pages.

Pastor, W.A. et al. (Jun. 2013). "TETonic Shift: Biological Roles of TET Proteins in DNA Demethylation and Transcription," Nat Rev Mol. Cell Biol. 14(6):341-356, 34 pages.

Peng, J. et al. (2015). "High-Throughput Screens in Mammalian Cells Using the CRISPR-Cas9 System," FEBS J. 282:2089-2096.

Perez, E.E. et al. (2008, e-pub. Jun. 29, 2008). "Establishment of HIV-1 Resistance in CD4+ T Cells by Genome Editing Using Zinc-Finger Nucleases," Nat. Biotechnol. 26:808-816.

Pfaffeneder, T. et al. (2011). "The Discovery of 5-Formylcytosine in Embryonic Stem Cell DNA," Angew Chem Int Ed Engl 50(31):7008-7012.

Phillips, E.R. et al. (2007). "DNA Double-Strand Break Repair and Development," Oncogene 26:7799-7808.

Potter, C.J. et al. (Apr. 13, 2010). "Splinkerette PCR for Mapping Transposable Elements in *Drosophila*," PLoS One 5(4):e10168, 9 pages.

Qian, L. et al. (May 2014, e-pub. Mar. 25, 2014). "Bidirectional Effect of Wnt Signaling Antagonist DKK1 on the Modulation of Anthrax Toxin Uptake," Science China Life Sciences 57(5):469-481.

Quinn, J.J. et al. (Jan. 2016). "Unique Features of Long Non-Coding RNA Biogenesis and Function," Nat. Rev. Genet. 17:47-62.

Ramakrishna, S. et al. (Feb. 26, 2014). "Surrogate Reporter-Based Enrichment of Cells Containing RNA-Guided Cas9 Nuclease-Induced Mutations," Nature Communications 5:3378, 10 pages.

Ratel, D. et al. (2006). "N6-Methyladenine: The Other Methylated Base of DNA," BioEssays 28:309-315.

Rathi, P. et al. (Jul. 18, 2016). "Isolation of Human Genomic DNA Sequences With Expanded Nucleobase Selectivity," J Am Chem Soc 138(31):9910-9918.

Ren, Q. et al. (Mar. 9, 2015). "A Dual-Reporter System for Real-Time Monitoring and High-throughput CRISPR/Cas9 Library Screening of the Hepatitis C Virus," Scientific Reports 5:8865, 7 pages.

Richardson, C.D. et al. (2016, e-pub. Jan. 20, 2016). "Enhancing Homology-Directed Genome Editing by Catalytically Active and Inactive CRISPR-Cas9 Using Asymmetric Donor DNA," Nat. Biotechnol., 7 pages.

Rinn, J.L. et al. (2012). "Genome Regulation by Long Noncoding RNAs," Annu. Rev. Biochem 81:145-166, 25 pages.

Robinson, M.D. et al. (2008, e-pub. Aug. 29, 2007). "Small-Sample Estimation of Negative Binomial Dispersion, With Applications to SAGE Data," Biostatistics 9:321-332.

(56) References Cited

OTHER PUBLICATIONS

Sakuma, T. et al. (2016, e-pub. Dec. 17, 2015). "MMEJ-Assisted Gene Knock-In Using TALENs and CRISPR-Cas9 With the PITCh Systems," Nat. Protoc. 11(1):118-133.

Sambrook, J. et al. (1989). Molecular Cloning: A Laboratory Manual, 3rd Ed. 29 pages.

Sambrook, J. et al. (2001). Molecular Cloning: A Laboratory Manual Cold Spring Harbor Laboratory Press, Cold Spring Harbor, N.Y., 3rd ed., 1 page, Table of Contents.

Sanjana, N. (Mar. 19, 2014). "Human and Mouse Non-Targeting Guides From GeCKOV2 Library," SanjanaLab, 5 pages.

Savić, N. et al. (2016). "Advances in Therapeutic CRISPR/Cas9 Genome Editing," Translational Research: The Journal of Laboratory and Clinical Medicine 168:15-21.

Schmid-Burgk. J.L. et al. (Jul. 28, 2016). "CRISPaint Allows Modular Base-Specific Gene Tagging Using a Ligase-4-Dependent Mechanism," Nature Communications 7(12338):1-12.

Schmierer, B. et al. (2017, e-pub. Oct. 9, 2017). "CRISPR/Cas9 Screening Using Unique Molecular Identifiers," Molecular Systems Biology 13:945, 8 pages.

Seed, B. (1987). "An LFA-3 cDNA Encodes a Phospholipid-Linked Membrane Protein Homologous to Its Receptor CD2," Nature 329:840-842.

Shalem, O. et al. (Jan. 3, 2014). "Genome-Scale CRISPR-Cas9 Knockout Screening in Human Cells," Science 343:84-87.

Shechner, D.M. et al. (2015, e-pub. Jun. 1, 2015). "Multiplexable, Locus-Specific Targeting of Long RNAs With CRISPR-Display," Nat Methods 12:664-670.

Steegmaier, M. et al. (Feb. 20, 2007). "BI 2536, A Potent and Selective Inhibitor of Polo-Like Kinase 1, Inhibits Tumor Growth In Vivo," Curr. Biol. 17:316-322.

Suzuki, E. et al. (Dec. 22, 2011). "Molecular Mechanisms of Bortezomib Resistant Adenocarcinoma Cells," PLoS One 6(12):e27996, 11 pages.

Taggart, A.J. et al. (2012). "Large-Scale Mapping of Branchpoints in Human Pre-mRNA Transcripts In Vivo," Nat. Struct. Mol. Biol. 19(7):719-721, 9 pages.

Tahiliani, M. et al. (May 15, 2009). "Conversion of 5-Methylcytosine to 5-Hydroxymethylcytosine in Mammalian DNA by MLL Partner TET1," Science 324(5929):930-935, 11 pages.

Tan, Y.Y. et al. (Aug. 15, 1989). "In Vitro Evaluation of 6-Thioguanine and Alpha-Interferon as a Therapeutic Combination in HL-60 and Natural Killer Cells," Cancer Res. 49:4431-4434.

Tao, L. et al. (2016). "Frizzled Proteins Are Colonic Epithelial Receptors for C. difficile Toxin B," Nature 538:350-355.

Tsjui, S. et al. (2016). "Sequence-Specific Recognition of Methylated DNA by an Engineered Transcription Activator-Like Effector Protein," Chem. Commun. 52:14238-14241.

Uren, A.G. et al. (2009, e-pub. Apr. 30, 2009). "A High-Throughput Splinkerette-PCR Method for the Isolation and Sequencing of Retroviral Insertion Sites," Nat. Protoc. 4(5):789-798.

Valton, J. et al. (Nov. 9, 2012). "Overcoming Transcription Activator-Like Effector (TALE) DNA Binding Domain Sensitivity to Cytosine Methylation," J Biol Chem 287(46):38427-38432.

Van Overbeek, M. et al. (Aug. 18, 2016). "DNA Repair Profiling Reveals Nonrandom Outcomes at Cas9-Mediated Breaks," Mol. Cell 63:1-14.

Wacker, S.A. et al. (Mar. 2012). "Using Transcriptome Sequencing to Identify Mechanisms of Drug Action and Resistance," Nat. Chem. Biol. 8:235-237.

Wang, T. et al. (Jan. 3, 2014). "Genetic Screens in Human Cells Using the CRISPR-Cas9 System," Science 343:80-84.

Wang, T. et al. (Nov. 27, 2015). "Identification and Characterization of Essential Genes in the Human Genome," Science 350(6264):1096-1101.

Warf, M.B. et al. (2010). "Role of RNA Structure in Regulating Pre-mRNA Splicing," Trends Biochem. Sci. 35:169-178, 21 pages.

Wei, W. et al. (Mar. 24, 2006). "The LDL Receptor-Related Protein LRP6 Mediates Internalization and Lethality of Anthrax Toxin," Cell 124:1141-1154.

Wion, D. (Mar. 2006). "N6-Methyl-Adenine: An Epigenetic Signal for DNA-Protein Interactions," Nature Reviews Microbiology 4:183-192.

Wu, H. et al. (Sep. 2015). "Charting Oxidized Methylcytosines at Base Resolution," Nat Struct Mol Biol 22(9):656-661, 14 pages.

Xu, H. et al. (2015). "Sequence Determinants of Improved CRISPR sgRNA Design," Genome Res. 25:1147-1157.

Yang, J. et al. (2016). "Assembly of Customized TAL Effectors Through Advanced ULtiMATE System." TALENs: Methods and Protocols pp. 49-60.

Yang, J. et al. (May 2014) Complete Decoding of TAL Effectors for DNA Recognition, Cell Research 24(5):628-631.

Yang, J. et al. (Sep. 27, 2013). "ULtiMATE System for Rapid Assembly of Customized TAL Effectors," PLoS One 8(9):e75649, 8 pages.

Yin, B. et al. (Jul. 2007). "PCR-Based Procedures to Isolate Insertion Sites of DNA Elements," Biotechniques 43(1):79-84.

Yu, C. et al. (Feb. 5, 2015). "Small Molecules Enhance CRISPR Genome Editing in Pluripotent Stem Cells," Cell Stem Cell 16:142-147.

Yu, M. et al. (Jun. 8, 2012). "Base-Resolution Analysis of 5-Hydroxymethylcytosine in the Mammalian Genome," Cell 149(6):1368-1380, 23 pages.

Yuan, P. et al. (2015, e-pub. Dec. 30, 2014). "Chondroitin Sulfate Proteoglycan 4 Functions as the Cellular Receptor for Clostridium difficile Toxin B," Cell Res 25:157-168.

Zhang, G. et al. (May 7, 2015). "N6-Methyladenine DNA Modification in *Drosophila*," Cell 161:1-14.

Zhang, Y. et al. (2017, e-pub. Oct. 12, 2017). "Deciphering TAL Effectors for 5-Methylcytosine and 5-Hydroxymethylcytosine Recognition," Nature Communications, 8(1):1-9.

Zhou, Y. et al. (2016, e-pub. Nov. 14, 2016). "Simultaneous Generation of Multi-Gene Knockouts in Human Cells," FEBS Letters 590:4343-4353.

Zhou, Y. et al. (2017, e-pub. Jan. 13, 2017). "Painting a Specific Chromosome With CRISPR/Cas9 for Live-Cell Imaging," Cell Res. 27:298-301, 4 pages.

Zhou, Y. et al. (May 22, 2014). "High-Throughput Screening of a CRISPR/Cas9 Library for Functional Genomics in Human Cells," Nature 509:487-491.

Zhu, S. et al. (2017). "Genome-Wide CRISPR/Cas9 Screening for High-Throughput Functional Genomics in Human Cells," Methods Mol Biol 1656:175-181.

Zhu, S. et al. (Dec. 2016). "Genome-Scale Deletion Screening of Human Long Non-Coding RNAs Using a Paired-Guide RNA CRISPR-Cas9 Library," Nat Biotechnol 34(12):1279-1286.

International Search Report, dated May 7, 2018, for PCT Application No. PCT/CN2017/095988, English Translation, 3 pages.

\* cited by examiner

TALE RVD SPECIFICALLY RECOGNIZING DNA BASE MODIFIED BY METHYLATION AND APPLICATION THEREOF

CROSS REFERENCE TO RELATED APPLICATIONS

This application is a National Phase application under 35 U.S.C. § 371 of International Application No. PCT/CN2017/095988, filed Aug. 4, 2017, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922001300SUBSEQLIST.TXT, date recorded: Nov. 2, 2020, size: 6 KB).

FIELD OF THE INVENTION

The present invention relates to techniques for regulating, editing and detecting genes by using DNA binding proteins.

BACKGROUND OF THE INVENTION

Transcription activator-like effectors (TALEs) are virulence factors from plant pathogenic bacteria *Xanthomonas*, and can reprogram the eukaryotic genome (1, 2). TALEs contains a DNA binding domain consisting of a variable number of tandem repeats (3). Each repeat comprises a consensus sequence of 33 to 35 amino acid residues, except for two hypervariable amino acids at positions 12 and 13 (repeat-variable diresidues or RVDs) (4,5). The recognition of DNA by a TALE protein is mediated by tandem repeats which target to nucleotides through their RVDs and bind to DNA in a sequence-specific manner. RVDs determine nucleotide specificity (4,6). RVDs contact with DNA bases in a direct, sequence-specific manner. By virtue of the modular DNA-recognition property, TALEs can be fused with a functional domain, such as a transcription activator (7, 8), a repressor (9, 10), or an endonuclease (11, 12), and is called a programmable genome editing tool. In the existing researches, the RVD-DNA recognition codes were partially deciphered by using experimental and computational approaches (4, 6); and it was found that the four most commonly used RVDs of NI, NG, HD, and NN preferentially binds to A, T, C, and G/A, respectively (4, 6).

Besides the four canonical deoxyribonucleotides, a mammalian genome also contains modified DNA bases. For instance, 5-methylcytosine (5mC) known as the fifth DNA base, is an important epigenetic marker that regulates gene expression (FIG. 1A) (15, 16). 5mC can be sequentially oxidized by the ten-eleven translocation (TET) family proteins to produce 5-hydroxymethylcytosine (5hmC), 5-formylcytosine (5fC) and 5-carboxylcytosine (5caC), the latter two are substrates of thymine DNA glycosylase and are eventually restored to unmodified cytosines (17, 22). 5hmC constitutes ~1%-10% of the modified cytosines and is believed to be a stable epigenetic mark; dysregulation of 5hmC is frequently observed in cancer.

In addition to methylation on cytosine, another common DNA methylation, N6-methyladenine (6 mA), plays an important role in prokaryotic cells as a covalent modification of adenine in DNA and involves in the regulation of multiple biological pathways, including resisting foreign DNA invasion as part of a restriction-modification (RM) system, and regulating in DNA replication, mismatch repair, gene transcription, and transposition etc. (41, 47). However, there are relatively few studies on 6 mA in eukaryotes, and the role of 6 mA in epigenetics is not very clear (46).

Three articles of Cell magazine in 2015 reported 6 mA in the genomes of eukaryotes such as *Chlamydomonas*, Nematodes and *Drosophila* (42, 43, 48). In the determination of the position of 6-methyladenine in *Chlamydomonas reinhardtii*, 6 mA is found being present in most genes of *Chlamydomonas reinhardtii*, and in most cases it appears in ApT two-base mode; in addition, the enrichment of 6 mA at the transcriptional start site is associated with active gene expression (42). According to the research of *Drosophila melanogaster* and *Caenorhabditis elegans*, 6 mA is likely to play an important role in the regulation of differentiation and development (48). It is found that 6 mA methylation- and demethylation-related enzymes are conserved in evolution, and 6 mA is likely to be distributed in other eukaryotes (43). Until 2016, Koziol et al. proved the presence of 6 mA in the genomes of vertebrates, including different tissues of *Xenopus laevis*, and tissues or cell lines of mouse and human. The abundance of 6 mA modification in vertebrates is very low. It is found that, unlike in *Chlamydomonas* and *Drosophila*, 6 mA are widely distributed in regions other than exons in *Xenopus* and mouse genomes, and show certain regularity of sequence motifs, indicating that 6 mA modification may have different functions in different eukaryotes (44). The distribution of 6 mA epigenetic modification in higher organisms and its role and mechanism in the development of cells and individuals need to be further studied.

TALE proteins were reported to recognize modified DNA bases (24-26). For instance, NG or N* ('*' represents the deletion of the 13th amino acid) was reported to recognize 5mC in the cognate DNA (25, 27-31); the combination of NG/N* and HD was used to discriminate 5mC/5hmC from C in an in vitro assay (32). A recent study also reported that a TALE protein with truncated repeat loops (G*, S*, and T*) can bind to C, 5mC, 5hmC, 5fC, and 5caC with similar affinities (33, 34). In the crystal structure of TALE-DNA complex, the RVD loop contacts with the DNA duplex major groove, in which the first residue stabilizes the proper loop conformation and the second residue makes a direct base-specific contact (35, 36). The full potential of RVDs in recognizing 5mC, 5hmC and 6 mA remains to be further explored.

SUMMARY OF THE INVENTION

RVDs with recognition preferences for 5mC, 5hmC and 6 mA and different binding properties to these epigenetic modifications are identified in the present invention. Methylation-dependent gene activation, efficient genome editing, and targeted detection of 5hmC can be achieved by using these RVDs.

According to one aspect of the present invention, provided is an isolated DNA binding polypeptide containing TALEs, wherein the TALEs comprise one or more RVDs selected from:

HA or NA, which specifically recognizes 5mC;
FS, which specifically recognizes 5hmC;
N*, NG or KP, which recognizes both C and 5mC;
HV or KV, which recognizes both C and 5hmC;
K* or RG, which recognizes both 5mC and 5hmC;
G*, H*, R* or Y*, which recognizes all three of C, 5mC and 5hmC;

NP, FT, CV or CP, which specifically recognizes 6 mA; or

RI, NI, KI or HI, which specifically recognizes both A and 6 mA;

wherein * indicates the deletion of an amino acid at this position.

According to another aspect of the present invention, provided is a fusion protein, comprising a functional domain and TALEs, wherein TALEs comprise one or more RVDs selected from:

HA or NA, which specifically recognizes 5mC;

FS, which specifically recognizes 5hmC;

N*, NG, or KP, which recognizes both C and 5mC;

HV or KV, which recognizes both C and 5hmC;

K* or RG, which recognizes both 5mC and 5hmC;

G*, H*, R*, or Y*, which recognizes all three of C, 5mC, and 5hmC;

NP, FT, CV or CP, which specifically recognizes 6 mA; or

RI, NI, KI or HI, which recognizes both A and 6 mA;

wherein * indicates the deletion of an amino acid at this position.

In some embodiments, the functional domain is a functional domain for regulating gene expression, a functional domain for epigenetic modification, a functional domain for genome editing, or a fluorescent protein.

In some embodiments, the functional domain for regulating gene expression is a transcriptional activator, a transcriptional repressor, or a functional fragment thereof, wherein the functional domain for epigenetic modification is a methyltransferase, a demethylase, or a functional fragment thereof, and the functional domain for genome editing is a nuclease or a functional fragment thereof.

In some embodiments, the functional domain for genome editing is an endonuclease, preferably a FokI endonuclease, and more preferably a DNA cleavage domain of a FokI endonuclease.

According to another aspect of the present invention, provided is a polynucleotide encoding the DNA binding polypeptide described above or any of the fusion proteins described above.

According to another aspect of the present invention, provided is a vector comprising the polynucleotide described above.

According to another aspect of the present invention, provided is a host cell comprising the polynucleotide described above or the vector described above.

According to another aspect of the present invention, provided is use of a protein comprising TALE repeats domain in the preparation of a reagent for detecting a methylated base in a target sequence of a gene of interest, comprising:

(1) use of a protein comprising TALE repeats domain in the preparation of a reagent for detecting the methylated base 5mC in the target sequence of a gene of interest, wherein one or more RVDs of the TALE repeats domain are HA or NA;

(2) use of a protein comprising TALE repeats domain in the preparation of a reagent for detecting the methylated base 5hmC in the target sequence of a gene of interest, wherein one or more RVDs of the TALE repeats domain are FS; or (3) use of a protein comprising TALE repeats domain in the preparation of a reagent for detecting the methylated base 6 mA in the target sequence of a gene of interest, wherein one or more RVDs of the TALE repeats domain are NP, FT, CV or CP.

According to another aspect of the present invention, provided is use of the DNA binding polypeptide described above, any of the fusion proteins described above, the polynucleotide described above, or the vector described above or the host cell described above in the preparation of a reagent for targeting and binding to a target sequence in a gene of interest in a cell.

According to another aspect of the present invention, provided is use of any of the fusion proteins described above or the polynucleotide encoding said fusion protein in the preparation of a reagent for regulating expression of a gene of interest in a cell, wherein the functional domain comprised in the fusion protein is a functional domain for regulating gene expression.

In some embodiments, the functional domain for regulating gene expression is a transcriptional activator or a functional fragment thereof, or a transcriptional repressor or a functional fragment thereof.

According to another aspect of the present invention, provided is use of any of the fusion proteins described above or the polynucleotide encoding said fusion protein for the preparation of a reagent for genome editing of a gene of interest in a cell, wherein the functional domain comprised in the fusion protein is a functional domain for genome editing.

In some embodiments, the genome editing is nucleic acid cleavage, and the functional domain for genome editing is a nuclease or a functional fragment thereof, preferably an endonuclease or a functional fragment thereof, and more preferably a FokI endonuclease or a DNA cleavage domain thereof.

According to another aspect of the present invention, provided is use of any of the fusion proteins described above or the polynucleotide encoding said fusion protein in the preparation of a reagent for epigenetic modification of a gene of interest in a cell, wherein the functional domain comprised in the fusion protein is a functional domain for epigenetic modification.

In some embodiments, the functional domain for epigenetic modification is a methyltransferase, a demethylase, or a functional fragment thereof.

According to another aspect of the present invention, provided is a method for targeting and binding to a target sequence of a gene of interest in a cell, comprising: introducing the DNA binding polypeptide, any of the fusion proteins described above, or the polynucleotide described above into a cell, thereby the TALEs in the DNA binding polypeptide or the fusion protein binds to the target sequence of a gene of interest.

In some embodiments, in the method described above:

the TALEs in the DNA binding polypeptide or the fusion protein comprises an RVD selected from HA or NA, and the TALEs in the DNA binding polypeptide or fusion protein binds to the target sequence of a gene of interest only when the target sequence of the gene of interest has a 5mC at a recognition site of the RVD;

the TALEs in the DNA binding polypeptide or fusion protein comprises an RVD selected from FS, and the TALEs in the DNA binding polypeptide or fusion protein binds to the target sequence of a gene of interest only when the target sequence of the gene of interest has a 5hmC at a recognition site of the RVD;

the TALEs in the DNA binding polypeptide or fusion protein comprises an RVD selected from NP, FT, CV or CP, and the TALEs in the DNA binding polypeptide or fusion protein binds to the target sequence of a gene of interest only when the target sequence of the gene of interest has a 6 mA at a recognition site of the RVD;

the TALEs in the DNA binding polypeptide or fusion protein comprises an RVD selected from N*, NG or KP, and the methylation state of the specific base at a recognition site of the RVD in the target sequence of the gene of interest is not determined and may be C or 5mC;

the TALEs in the DNA binding polypeptide or fusion protein comprises an RVD selected from HV or KV, and the methylation state of the specific base at a recognition site of the RVD in the target sequence of the gene of interest is not determined and may be C or 5hmC;

the TALEs in the DNA binding polypeptide or fusion protein comprises an RVD selected from K* or RG, and the methylation state of the specific base at a recognition site of the RVD in the target sequence of the gene of interest is not determined and may be 5mC or 5hmC;

the TALEs in the DNA binding polypeptide or fusion protein comprises an RVD selected from G*, H*, R* or Y*, and the methylation state of the specific base at a recognition site of the RVD in the target sequence of the gene of interest is not determined and may be C, 5mC or 5hmC; or the TALEs in the DNA binding polypeptide or fusion protein comprises an RVD selected from RI, NI, KI or HI, and the methylation state of the specific base at a recognition site of the RVD in the target sequence of the gene of interest is not determined and may be A or 6 mA;

wherein * indicates the deletion of an amino acid at this position.

According to another aspect of the present invention, provided is a method for regulating expression of a gene of interest in a cell, comprising: introducing any of the fusion proteins described above, or the polynucleotide encoding said fusion protein into a cell, thereby the TALEs in the fusion protein bind to a target sequence of a gene of interest, thereby allowing expression of the gene of interest to be regulated by a functional domain in the fusion protein, wherein the functional domain regulates expression of the gene.

In some embodiments, in the method described above:

the TALEs in the fusion protein comprise an RVD selected from HA or NA, and the TALEs in the fusion protein bind to the target sequence of a gene of interest only when the target sequence of the gene of interest has a 5mC at a recognition site of the RVD;

the TALEs in the fusion protein comprise an RVD selected from FS, and the TALEs in the fusion protein bind to the target sequence of a gene of interest only when the target sequence of the gene of interest has a 5hmC at a recognition site of the RVD;

the TALEs in the fusion protein comprise an RVD selected from NP, FT, CV or CP, and the TALEs in the fusion protein bind to the target sequence of a gene of interest only when the target sequence of the gene of interest has a 6 mA at a recognition site of the RVD;

the TALEs in the fusion protein comprise an RVD selected from N*, NG or KP, and the methylation state of the specific base at a recognition site of the RVD in the target sequence of the gene of interest is not determined and may be C or 5mC;

the TALEs in the fusion protein comprise an RVD selected from HV or KV, and the methylation state of the specific base at a recognition site of the RVD in the target sequence of the gene of interest is not determined and may be C or 5hmC;

the TALEs in the fusion protein comprise an RVD selected from K* or RG, and the methylation state of the specific base at a recognition site of the RVD in the target sequence of the gene of interest is not determined and may be 5mC or 5hmC;

the TALEs in the fusion protein comprise an RVD selected from G*, H*, R* or Y*, and the methylation state of the specific base at a recognition site of the RVD in the target sequence of the gene of interest is not determined and may be C, 5mC or 5hmC; or the TALEs in the fusion protein comprise an RVD selected from RI, NI, KI or HI, and the methylation state of the specific base at a recognition site of the RVD in the target sequence of the gene of interest is not determined and may be A or 6 mA;

wherein * indicates the deletion of an amino acid at this position.

In some embodiments, in the method described above, the functional domain for regulating gene expression is a transcriptional activator or a functional fragment thereof, or a transcriptional repressor or a functional fragment thereof.

According to another aspect of the present invention, provided is a method for editing a gene of interest in a cell, comprising: introducing any of the fusion proteins described above, or the polynucleotide encoding said fusion protein into a cell, thereby the TALEs in the fusion protein bind to a target sequence of a gene of interest, thereby allowing the gene of interest to be edited by a functional domain in the fusion protein, wherein the functional domain is a functional domain for genome editing.

In some embodiments, in the method described above:

the TALEs in the fusion protein comprise an RVD selected from HA or NA, and the TALEs in the fusion protein bind to the target sequence of a gene of interest only when the target sequence of the gene of interest has a 5mC at a recognition site of the RVD;

the TALEs in the fusion protein comprise an RVD selected from FS, and the TALEs in the fusion protein bind to the target sequence of a gene of interest only when the target sequence of the gene of interest has a 5hmC at a recognition site of the RVD;

the TALEs in the fusion protein comprise an RVD selected from NP, FT, CV or CP, and the TALEs in the fusion protein bind to the target sequence of a gene of interest only when the target sequence of the gene of interest has a 6 mA at a recognition site of the RVD;

the TALEs in the fusion protein comprise an RVD selected from N*, NG or KP, and the methylation state of the specific base at a recognition site of the RVD in the target sequence of the gene of interest is not determined and may be C or 5mC;

the TALEs in the fusion protein comprise an RVD selected from HV or KV, and the methylation state of the specific base at a recognition site of the RVD in the target sequence of the gene of interest is not determined and may be C or 5hmC;

the TALEs in the fusion protein comprise an RVD selected from K* or RG, and the methylation state of the specific base at a recognition site of the RVD in the target sequence of the gene of interest is not determined and may be 5mC or 5hmC;

the TALEs in the fusion protein comprise an RVD selected from G*, H*, R* or Y*, and the methylation state of the specific base at a recognition site of the RVD in the target sequence of the gene of interest is not determined and may be C, 5mC or 5hmC; or the TALEs in the fusion protein comprise an RVD selected from RI, NI, KI or HI, and the methylation state of the specific base at a recognition site of the RVD in the target sequence of the gene of interest is not determined and may be A or 6 mA;

wherein * indicates the deletion of an amino acid at this position.

In some embodiments, in the above method, the genome editing is nucleic acid cleavage, and the functional domain for genome editing is a nuclease or a functional fragment thereof, preferably an endonuclease or a functional fragment thereof, and more preferably a FokI endonuclease or a DNA cleavage domain thereof.

According to another aspect of the present invention, provided is a method for epigenetic modification of a gene of interest in a cell, comprising: introducing the fusion protein of any of claims 2-3 or the polynucleotide encoding said fusion protein into a cell, thereby the TALEs in the fusion protein bind to a target sequence of a gene of interest, thereby allowing the epigenetic modification of the gene of interest through a functional domain in the fusion protein, wherein the functional domain is a functional domain for epigenetic modification.

In some embodiments, in the method described above:

the TALEs in the fusion protein comprise an RVD selected from HA or NA, and the TALEs in the fusion protein bind to the target sequence of a gene of interest only when the target sequence of the gene of interest has a 5mC at a recognition site of the RVD;

the TALEs in the fusion protein comprise an RVD selected from FS, and the TALEs in the fusion protein bind to the target sequence of a gene of interest only when the target sequence of the gene of interest has a 5hmC at a recognition site of the RVD;

the TALEs in the fusion protein comprise an RVD selected from NP, FT, CV or CP, and the TALEs in the fusion protein bind to the target sequence of a gene of interest only when the target sequence of the gene of interest has a 6 mA at a recognition site of the RVD;

the TALEs in the fusion protein comprise an RVD selected from N*, NG or KP, and the methylation state of the specific base at a recognition site of the RVD in the target sequence of the gene of interest is not determined and may be C or 5mC;

the TALEs in the fusion protein comprise an RVD selected from HV or KV, and the methylation state of the specific base at a recognition site of the RVD in the target sequence of the gene of interest is not determined and may be C or 5hmC;

the TALEs in the fusion protein comprise an RVD selected from K* or RG, and the methylation state of the specific base at a recognition site of the RVD in the target sequence of the gene of interest is not determined and may be 5mC or 5hmC;

the TALEs in the fusion protein comprise an RVD selected from G*, H*, R* or Y*, and the methylation state of the specific base at a recognition site of the RVD in the target sequence of the gene of interest is not determined and may be C, 5mC or 5hmC; or the TALEs in the fusion protein comprise an RVD selected from RI, NI, KI or HI, and the methylation state of the specific base at a recognition site of the RVD in the target sequence of the gene of interest is not determined and may be A or 6 mA;

wherein * indicates the deletion of an amino acid at this position.

In some embodiments, in the method described above, the functional domain for epigenetic modification is a methyl-transferase, a demethylase, or a functional fragment thereof.

According to another aspect of the present invention, provided is a method for labeling a chromosome of a living cell, comprising: introducing any of the fusion proteins described above, or the polynucleotide encoding said fusion protein into a cell, thereby the TALEs in the fusion protein bind to a target sequence of a gene of interest, wherein the functional domain is a fluorescent protein, and fluorescent labeling of the target sequence is achieved by binding the TALEs in the fusion protein to the target sequence of the gene of interest.

In some embodiments, in the method described above:

the TALEs in the fusion protein comprise an RVD selected from HA or NA, and the TALEs in the fusion protein bind to the target sequence of a gene of interest only when the target sequence of the gene of interest has a 5mC at a recognition site of the RVD;

the TALEs in the fusion protein comprise an RVD selected from FS, and the TALEs in the fusion protein bind to the target sequence of a gene of interest only when the target sequence of the gene of interest has a 5hmC at a recognition site of the RVD;

the TALEs in the fusion protein comprise an RVD selected from NP, FT, CV or CP, and the TALEs in the fusion protein bind to the target sequence of a gene of interest only when the target sequence of the gene of interest has a 6 mA at a recognition site of the RVD;

the TALEs in the fusion protein comprise an RVD selected from N*, NG or KP, and the methylation state of the specific base at a recognition site of the RVD in the target sequence of the gene of interest is not determined and may be C or 5mC;

the TALEs in the fusion protein comprise an RVD selected from HV or KV, and the methylation state of the specific base at a recognition site of the RVD in the target sequence of the gene of interest is not determined and may be C or 5hmC;

the TALEs in the fusion protein comprise an RVD selected from K* or RG, and the methylation state of the specific base at a recognition site of the RVD in the target sequence of the gene of interest is not determined and may be 5mC or 5hmC;

the TALEs in the fusion protein comprise an RVD selected from G*, H*, R* or Y*, and the methylation state of the specific base at a recognition site of the RVD in the target sequence of the gene of interest is not determined and may be C, 5mC or 5hmC; or the TALEs in the fusion protein comprise an RVD selected from RI, NI, KI or HI, and the methylation state of the specific base at a recognition site of the RVD in the target sequence of the gene of interest is not determined and may be A or 6 mA;

wherein * indicates the deletion of an amino acid at this position.

According to another aspect of the present invention, provided is a method for detecting the presence of 5mC at a specific site of a target sequence in the genome of a cell, comprising:

(1) introducing a protein comprising TALEs into the cell, wherein the TALEs targets the target sequence, and in the TALEs the RVD identifying the specific site is HA or NA;

(2) introducing a nuclease into the cell, wherein the targeted cleavage site of the nuclease is located in the TALEs target sequence;

(3) detecting whether the target sequence is cleaved, thereby judging whether 5mC is present at the specific site of the target sequence; if the target sequence is not cleaved, then the TALEs bind to the target sequence, and the nuclease cannot bind to the target sequence and cleave it, thereby 5mC is present at the specific site; if the target sequence is cleaved, then the TALEs do not bind to the target sequence, and the nuclease binds to the target sequence and cleaves it, thereby 5mC is not present at the specific site.

According to another aspect of the present invention, provided is a method for detecting the presence of 5hmC at a specific site of a target sequence in the genome of a cell, comprising the steps of:

(1) introducing a protein comprising TALEs into the cell, wherein the TALEs target the target sequence, and in the TALEs the RVD identifying the specific site is FS;

(2) introducing a nuclease into the cell, wherein the targeted cleavage site of the nuclease is located in the TALEs target sequence;

(3) detecting whether the target sequence is cleaved, thereby judging whether 5hmC is present at the specific site of the target sequence; if the target sequence is not cleaved, then the TALEs bind to the target sequence, and the nuclease cannot bind to the target sequence and cleave it, thereby 5hmC is present at the specific site; if the target sequence is cleaved, then the TALEs do not bind to the target sequence, and the nuclease binds to the target sequence and cleaves it, thereby 5hmC is not present at the specific site.

According to another aspect of the present invention, provided is a method for detecting the presence of 6 mA at a specific site of a target sequence in the genome of a cell, comprising:

(1) introducing a protein comprising TALEs into the cell, wherein the TALEs target the target sequence, and in the TALEs the RVD identifying the specific site is NP, FT, CV or CP;

(2) introducing a nuclease into the cell, wherein the targeted cleavage site of the nuclease is located in the TALEs target sequence;

(3) detecting whether the target sequence is cleaved, thereby judging whether 6 mA is present at the specific site of the target sequence; if the target sequence is not cleaved, then the TALEs bind to the target sequence, and the nuclease cannot bind to the target sequence and cleave it, thereby 6 mA is present at the specific site; if the target sequence is cleaved, then the TALEs do not bind to the target sequence, and the nuclease binds to the target sequence and cleaves it, thereby 6 mA is not present at the specific site.

In some embodiments, the nuclease is an endonuclease.

In some embodiments, the nuclease is a Cas9 nuclease, and the Cas9 nuclease and sgRNA are co-introduced into the cell in step (1).

(a) A heat map summarizing the screening data of 5mC and 5hmC. For easy comparison, the results for canonical DNA fragments of C and T reporters are also shown. EGFP activities of different reporter DNA fragments are coded by using different colors representing identities of the reporters, and the brightness of the colors indicates the fold induction of reporter DNA fragments by normalized to the basal levels. The single-letter abbreviations for the amino acids are used.

(b) The results of the experiment of the selected RVDs with ability to recognize 5mC and 5hmC are selected from the preliminary screening results in FIG. (a), in particular, some RVDs showing higher EGFP fold induction for 5mC and 5hmC reporter systems are selected to perform 3 repeated experiments for confirmation. The preference of RVDs for modified cytosine is shown in this panel. RVDs are divided into clusters according to base preferences, and each cluster is divided into groups by the 13th residue. The data are means±SD, n=3; *P<0.05, and **P<0.005.

Figure 3:
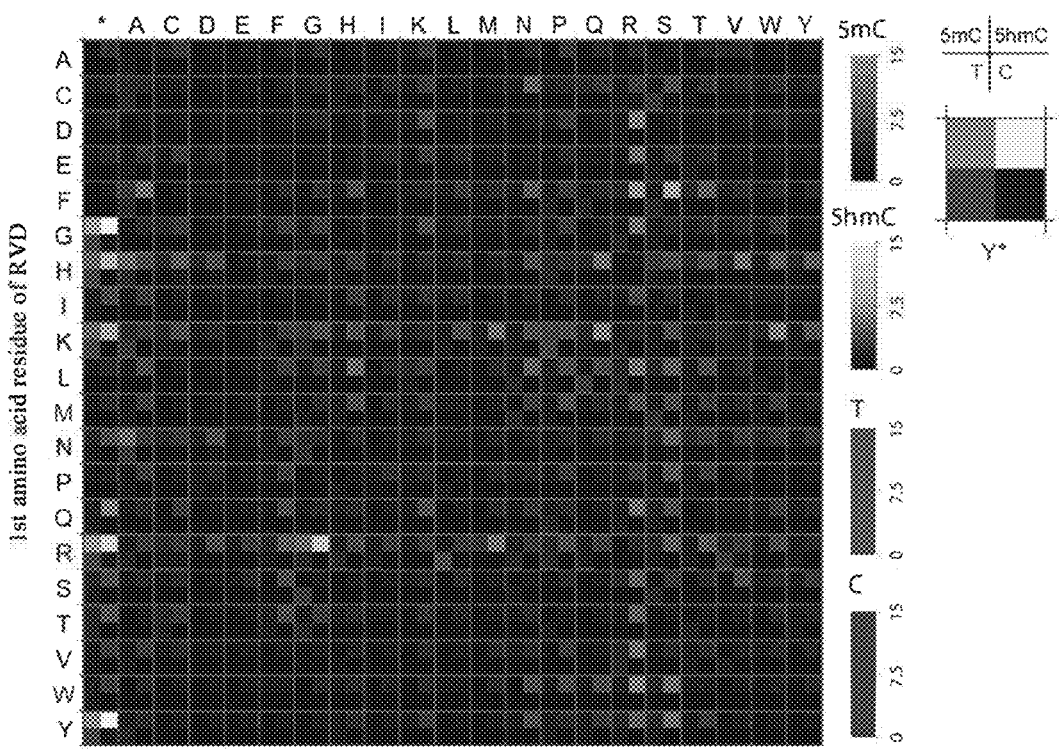
FIG. 3 shows a complete assessment of the efficiency and specificity of TALE RVD for 5mC and 5hmC.
Figure 3:
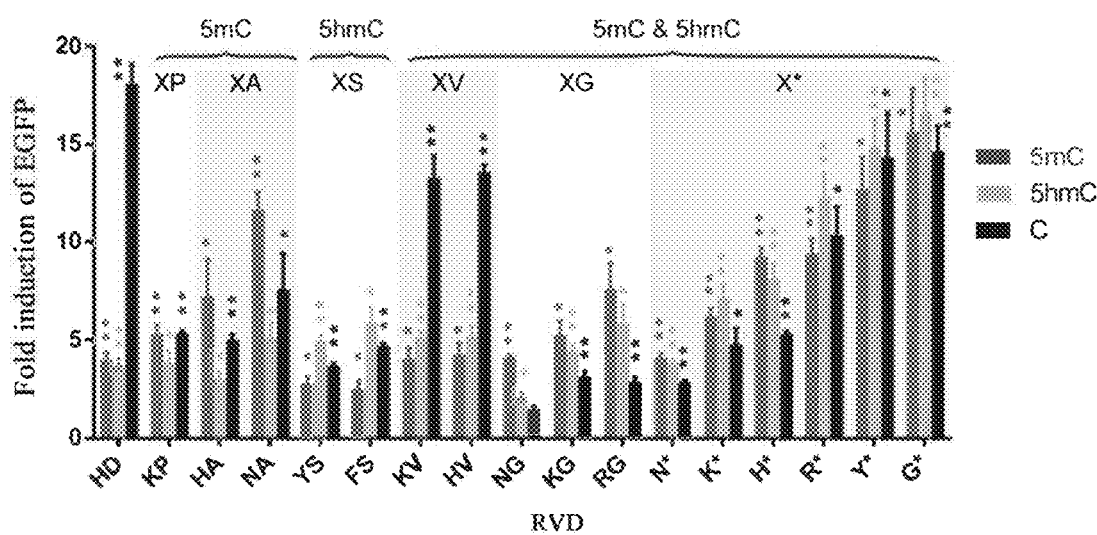
Figure 4:
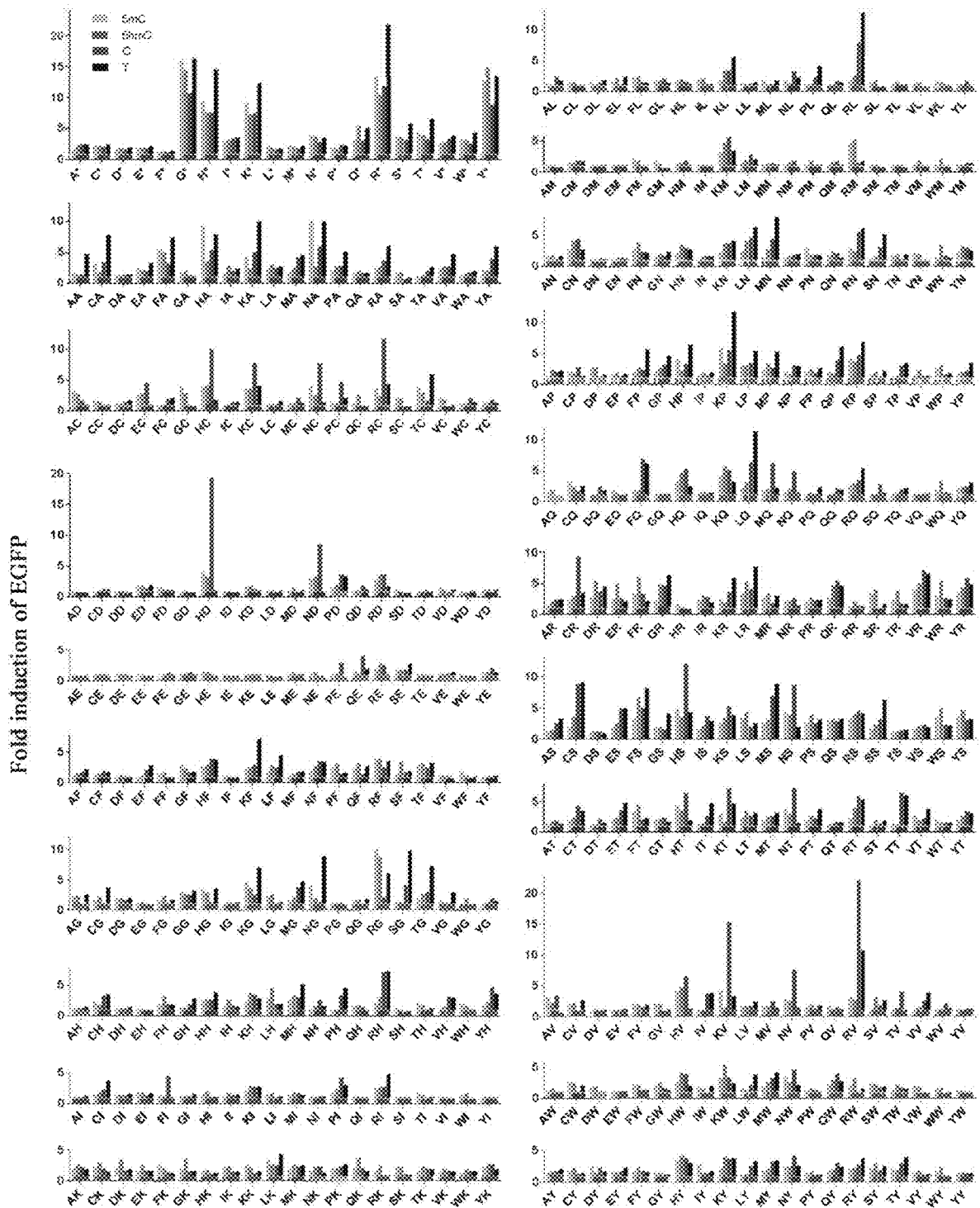

FIG. 4 shows the binding preferences of 420 TALE RVDs for modified cytosines. The data is corresponding to that of the heat map (FIG. 3a). The Y-axis is the fold induction of EGFP reporter, and the X-axis is the RVDs. The bar plot is categorized according to the first residue of RVD, and the data is listed alphabetically according to the second residue.

Figure 5:
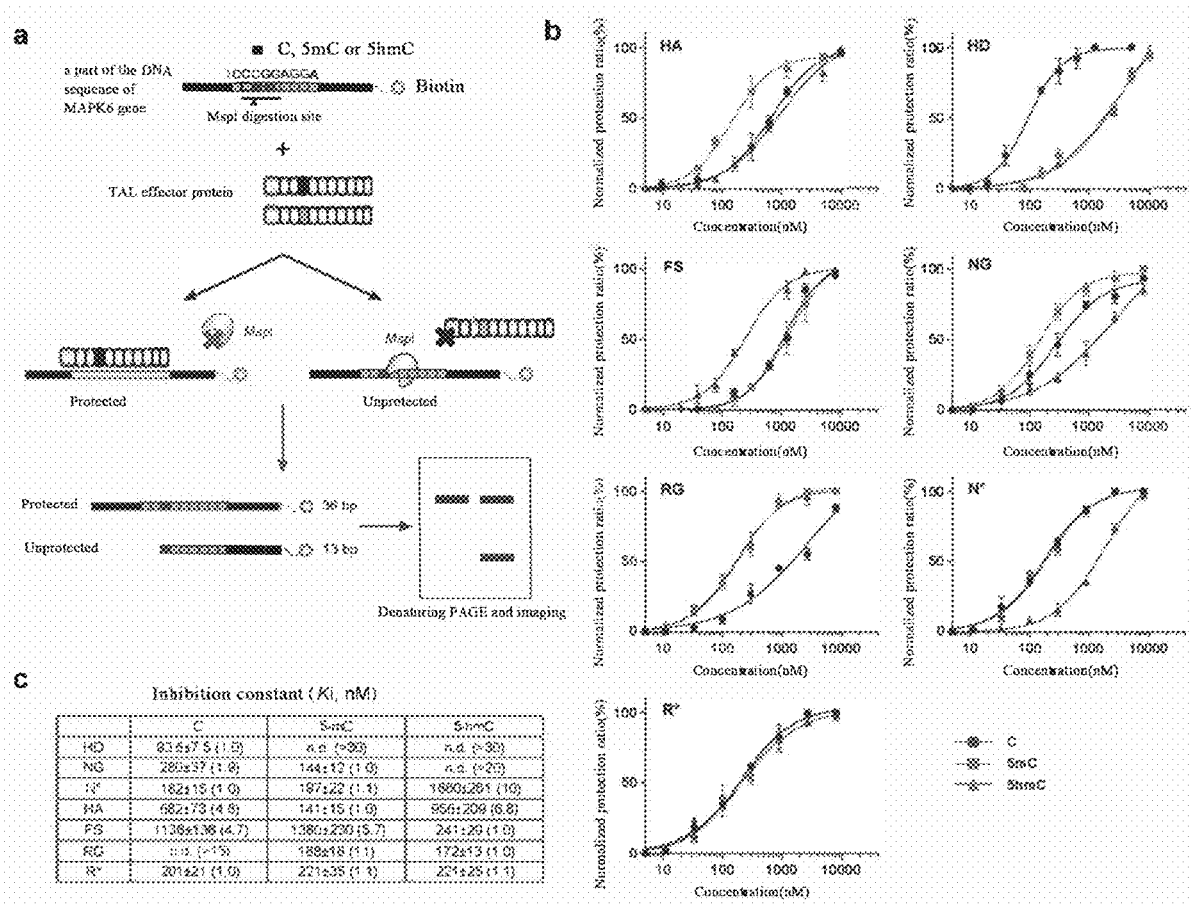

FIG. 5 shows the quantitative measurement of the DNA recognition of TALE RVDs by using an in vitro protection assay.

(a) Principle of in vitro protection assay. Briefly, the binding of TALE proteins (the TAL effector in this figure) to the DNA fragment of a specific sequence will block the MspI restriction endonuclease site, and inhibit the cleavage of an endonuclease, thereby resulting in a protected full-length band and a cleaved-DNA band during denaturing PAGE analysis. The protection efficiency for DNA reflects the binding efficiency of TALE proteins to DNA.

(b) The normalized protection efficiencies are obtained by measuring the uncleaved or protected DNA fragments, and they are fitted into protection curves of different TALE RVDs. The curves are fitted into a specific binding curve with Hill slope (GraphPad). All assays are replicated for 3 times.

(c) Inhibition constant calculated from (b). The ratio of each constant to the lowest inhibition constant of the same RVD is indicated within the parentheses. The inhibition constants of RVDs are obtained by getting the protection efficiency through the cleavage protection experiments of TALE proteins containing different RVDs with regard to C, 5mC and 5hmC, and then fitting the protection efficiency curves with GraphPad Prism 6 software and calculating the inhibition constants. The inhibition constants indicate the binding efficiencies of different RVDs for C, 5mC and 5hmC. The smaller inhibition constants indicate stronger protection efficiency of RVDs and stronger binding to the corresponding DNA fragment. As used herein, the lowest inhibition constant of the same RVD refers to the inhibition constant value of the group in which the RVD has the highest binding efficiency for C, 5mC and 5hmC.

Figure 6:
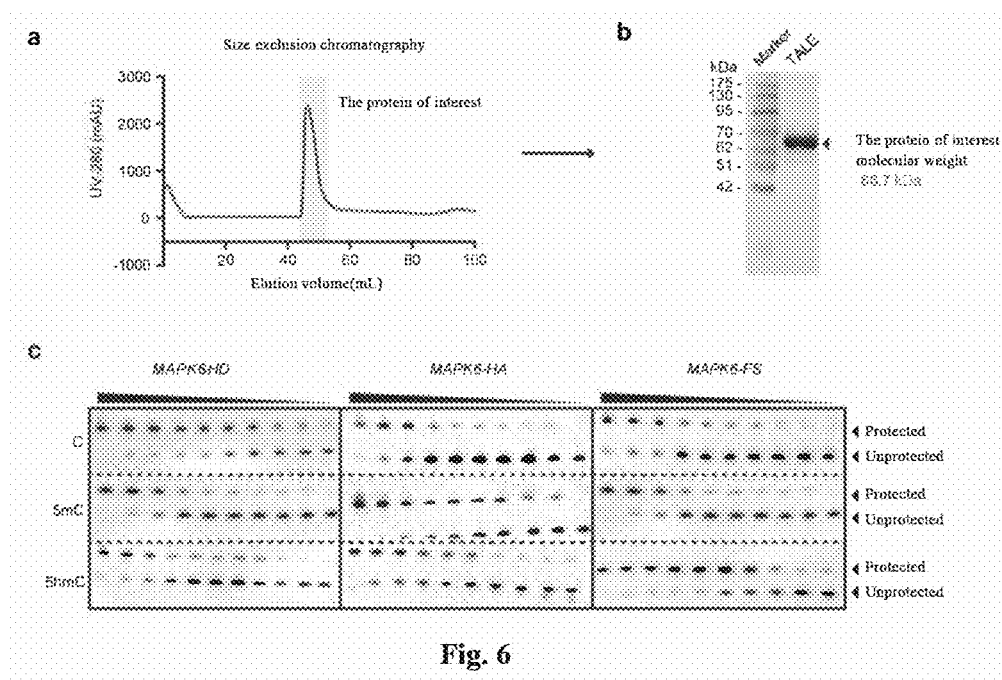

FIG. 6 shows the specific binding of different TALE RVDs to epigenetic cytosines in in vitro protection assay.
(a) A representative size exclusion chromatography of purified TALE proteins.
(b) SDS-PAGE analysis shows that the molecular weight of the purified TALE protein is correlated well with the calculated molecular weight.
(c) Representative gel images of in vitro protection assay. It can be seen from FIG. 6, MAPK6-HD may protect C with the highest efficiency, while HA protects 5mC and 5hmC with higher efficiency than that of unmodified C, and FS protects 5hmC with the highest efficiency.

Figure 7:
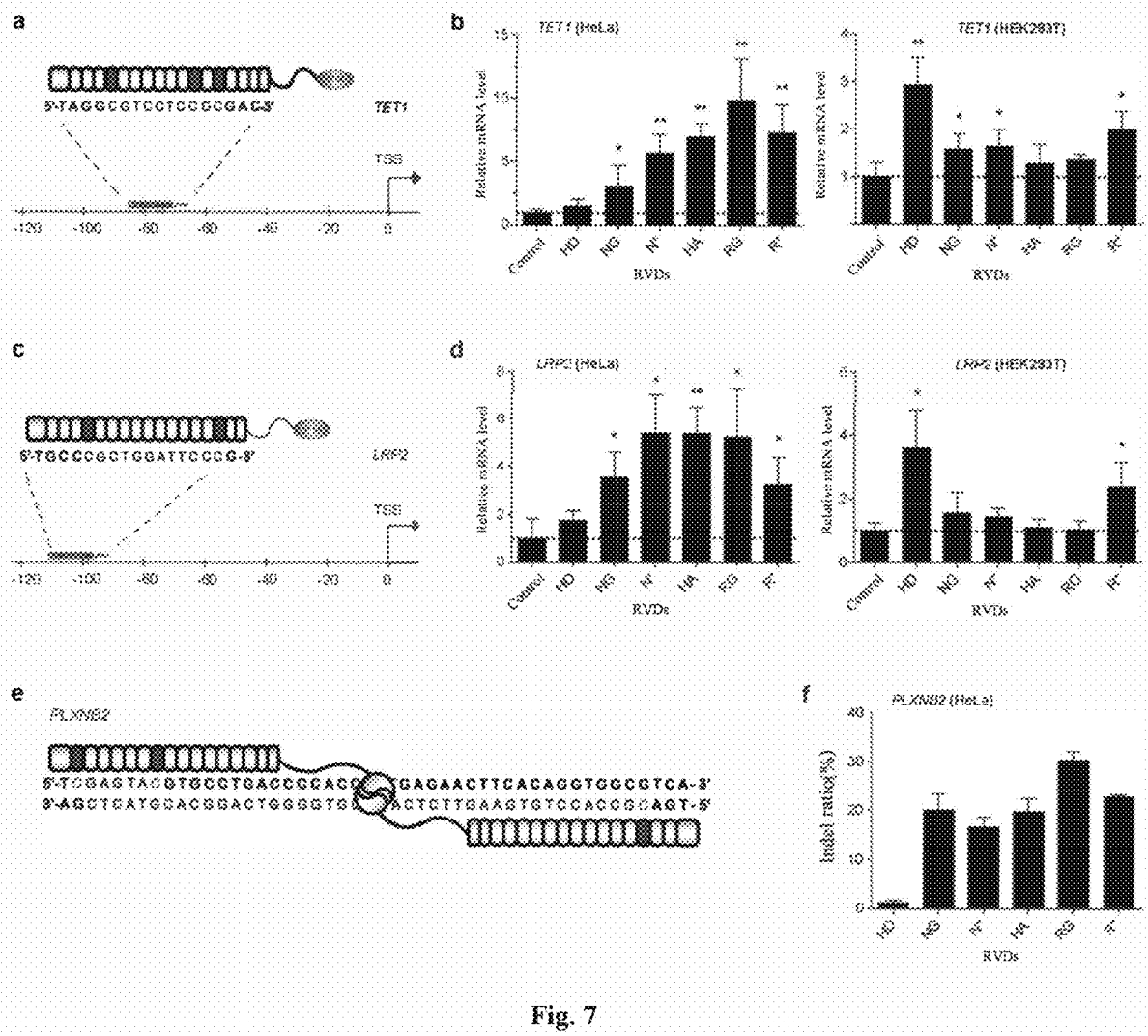

FIG. 7 shows the methylation-dependent gene expression activation and genome editing.
(a) $TALE_{TET1}$ targets to a 16 bp DNA sequence at ~80 bp upstream of the transcription start site (TSS) of the TET1 gene. All three CpGs (where C is indicated in black) in the region are highly methylated in HeLa cells but unmethylated in HEK293T cells.
(b) The relative mRNA level of TET in HeLa and HEK293T cells transfected with $TALE_{TET1}$ containing different RVDs.
(c) $TALE_{LRP2}$ targets to a 16 bp sequence at 100 bp upstream of the TSS of the LRP2 gene. Both the two CpGs in these two regions contain medium-level methylation in HeLa cells, but they are unmethylated in HEK293T cells.
(d) The relative mRNA level of LRP2 in HeLa and HEK293T cells transfected with $TALE_{LRP2}$ containing different RVDs.
(e) The position of TALEN (Transcription activator-like effector nuclease, TALEs fused with a FokI endonuclease) targeted sequence. The methylated CpGs are indicated in black.
(f) The genome editing efficiency of TALEN with different RVDs. The data are means±SD, n=3; *P<0.05, and **P<0.005.

Figure 8:
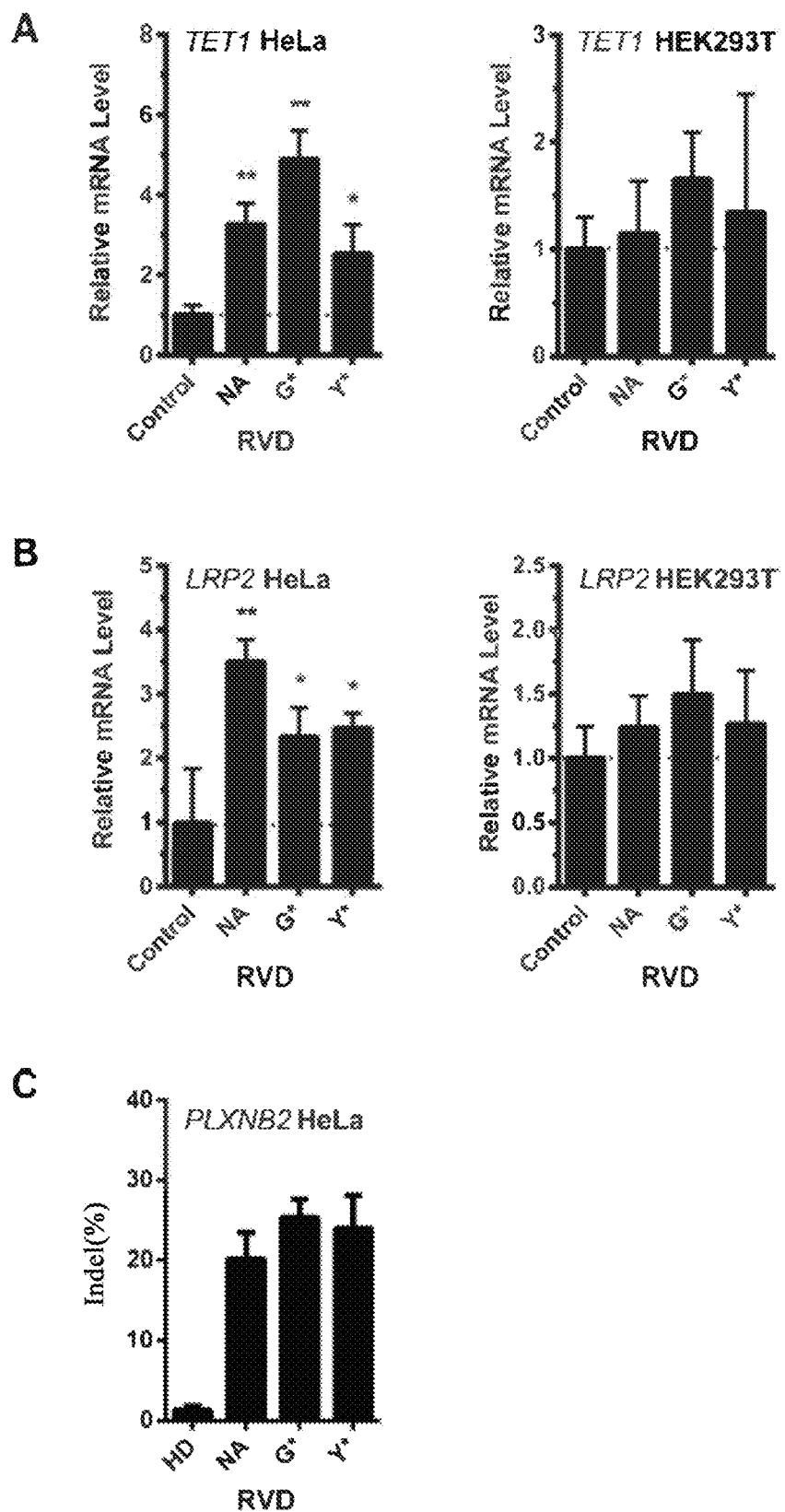

FIG. 8 shows the methylation-dependent gene expression activation and genome editing.
(a) The relative mRNA level of TET in HeLa and HEK293T cells transfected with $TALE_{TET1}$ containing RVDs NA, G* and Y*.
(b) The relative mRNA level of LRP2 in HeLa and HEK293T cells transfected with TALELRP2containing RVDs NA, G* and Y*.
(c) The genome editing efficiency of TALEN containing RVDs NA, G* and Y*. Data are means±SD, n=3; *P<0.05, and **P<0.005.

Figure 9:
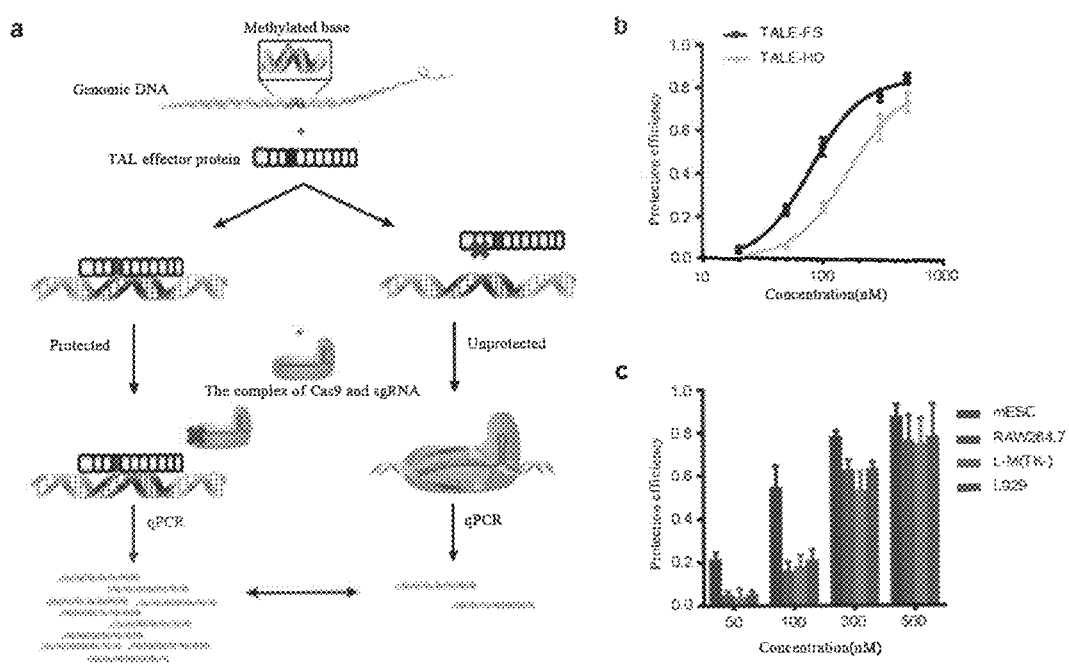

FIG. 9 shows the detection of 5hmC at single-base resolution in genomic DNA.
(a) Workflow of the detection of 5hmC at base-resolution by newly identified RVDs. Briefly, the targeted genomic region is protected by TALEs, against Cas9-mediated DNA cleavage.
(b) The protection efficiency of TALE-FS (black) and TALE-HD (gray) targeting a single 5hmC site of mESC genome.
(c) Protection efficiency of TALE-FS for a single 5hmC site in the genomic DNA of mESC, RAW264.7, L-M(TK-) and L929 cells. At this given site, mESC genome contains the highest 5hmC modification level among all of the cell lines.

Figure 10:
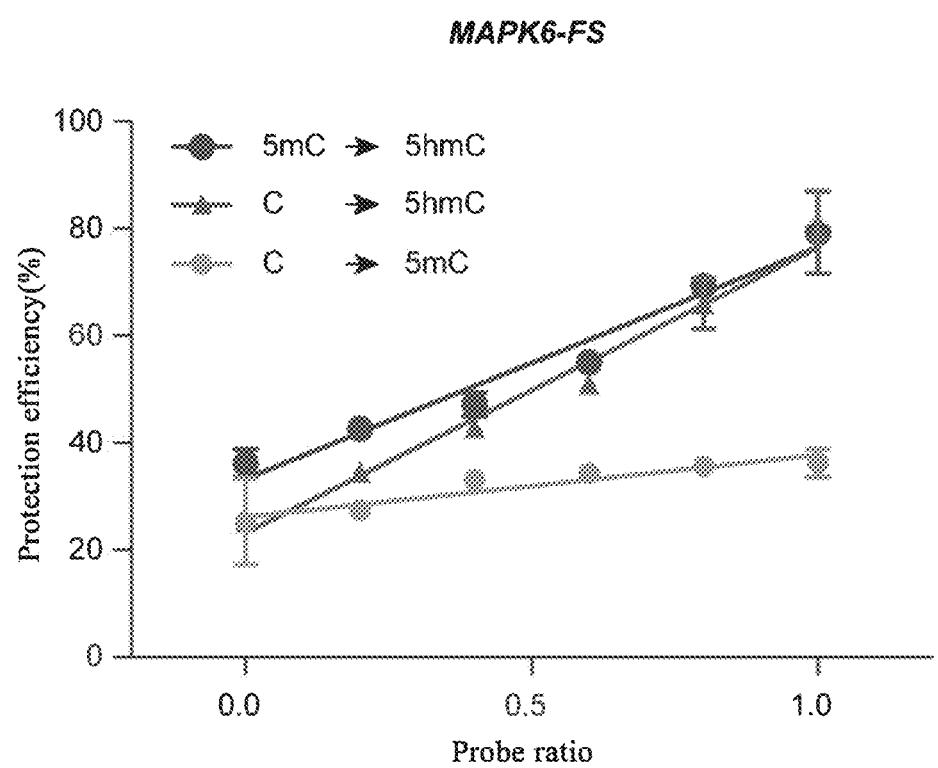

FIG. 10 shows the selective protection of 5hmC-containing DNA by TALE-FS. DNA containing 5mC, 5hmC and unmodified C (having the same sequence as MAPK6 gene) were pairwise mixed in different proportions. When the fraction of 5mC (gray circle) is increased, the protection efficiency is only slightly increased. When the fraction of 5hmC is increased (mixed with C and 5mC, dark circle and dark triangle), the protection efficiency is greatly increased, indicating the selective protection of 5hmC by RVD FS.

Figure 11:
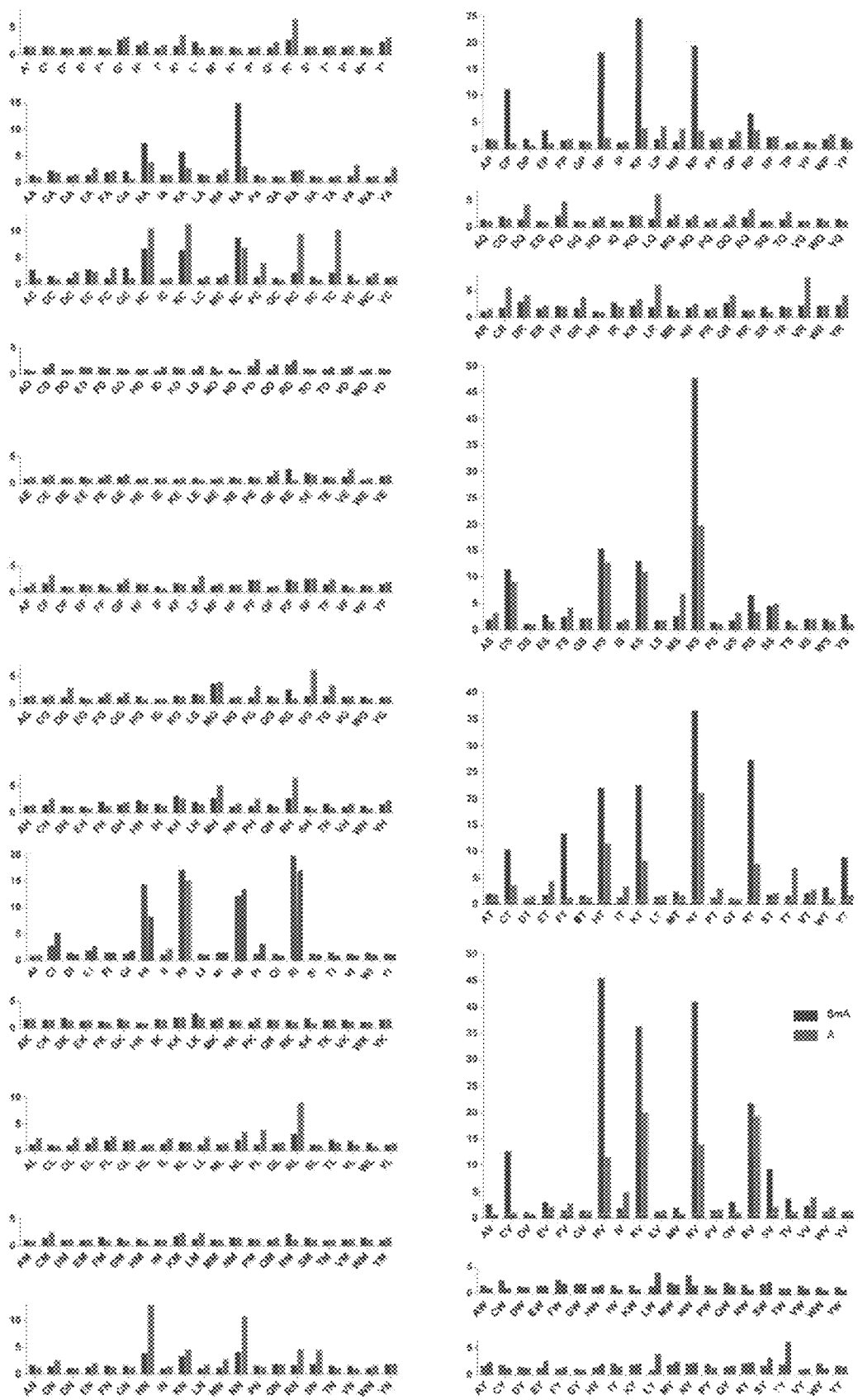

FIG. 11 shows the binding property of TALE-(XX')$_3$ to 6 mA and A.

Figure 12:
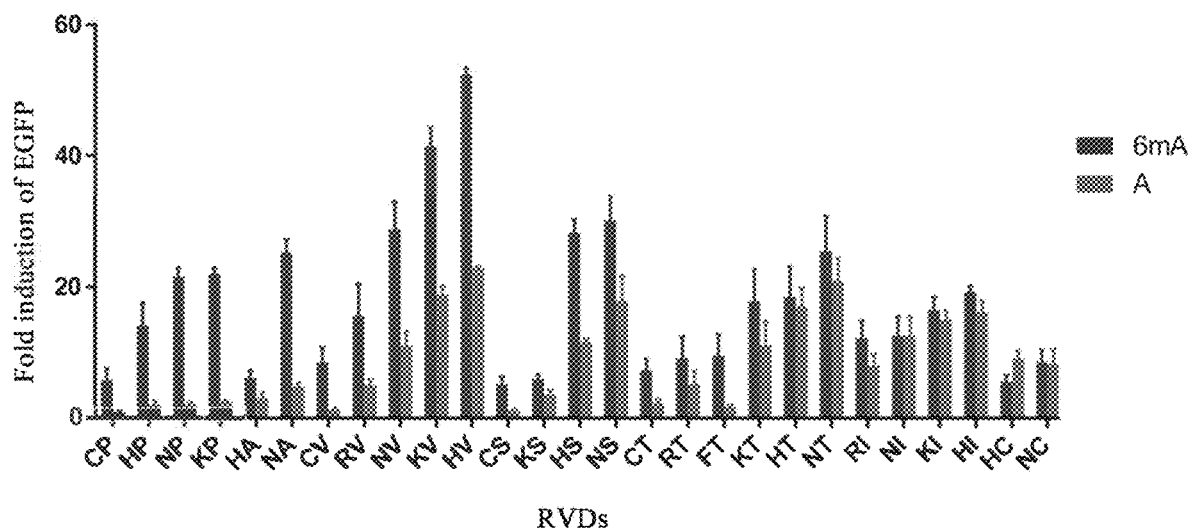

FIG. 12 shows the binding property of a portion of TALE-(XX')$_3$ to 6 mA and A. They are divided into groups according to the second amino acid of the RVDs, and ranked by the activation efficiency of the 6 mA reporting system from low to high in each group; the vertical axis is the fold activation of the EGFP in the reporting system, the gray corresponds to the A reporting system, the black corresponds to the 6 mA reporting system, and the horizontal axis is the RVDs; only data groups with the 6 mA mean values from the repeated experiments greater than 5 are shown. Data are means±s.d., n=3.

Figure 13:
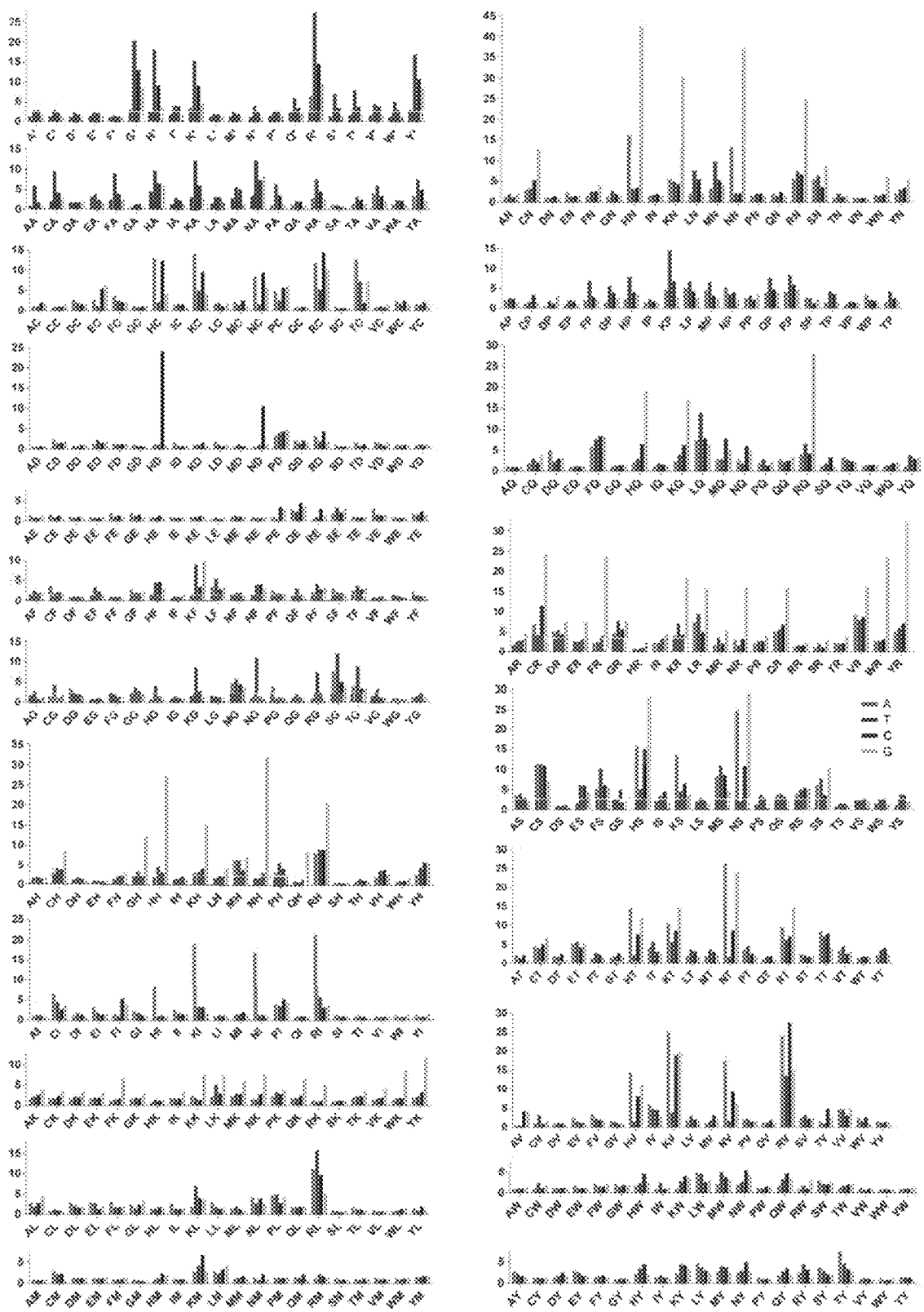

FIG. 13 shows the recognition efficiency of different RVDs for the A, T, C and G reporting systems.

DETAILED DESCRIPTION OF THE INVENTION

The invention shows that the binding of TALE protein to DNA is influenced by DNA base modification. The present invention identifies RVDs with specific binding preference to 5mC, 5hmC and/or 6 mA by studying 420 RVDs. 5mC, 5hmC and 6 mA are important epigenetic markers in higher eukaryotes. Methylome and hydroxymethylome do not interfere with base pairing; however, they are present in the major grooves of the DNA duplex and affect their interaction with the TALE proteins.

The structure of the TALE-DNA complex shows that the amino acid at position 13 is the only residue interacting directly with the DNA base of the sense strand, while the residue at position 12 serves to stabilize the proper loop conformation during base pair recognition (35, 36). The present invention demonstrates that a small amino acid (Gly and Ala) or deletion at position 13 increases the affinity for 5mC. This observation is consistent with previous findings that N* and NG (naturally recognizing T) can bind to 5mC. It is probably that the absence of a large side chain at position 13 may result in enough space to hold the methyl group of 5mC. However, there are exceptions for this general trend. For example, it is also observed in the present invention that the affinity of HG for 5mC is very weak. HG contains a smaller residue at position 13 than HD which is a natural conjugate of C. Interestingly, when His at position 12 is replaced by Arg (thus it turns to RG), a strong binding to 5mC is observed. In fact, RG also recognizes 5hmC. These observations indicate that the recognition of modifications by double residues may be more complex.

The present invention demonstrates the TALE-mediated methylation-dependent gene activation and genome editing of several hypermethylated genomic regions. As an important control, almost no gene activation is observed when the same region lacks cytosine methylation (in different cells). Thus, the RVDs discovered in the present invention provide such a potential: manipulating the gene of interest according to its modified state in vivo. It is known that there are many differentially methylated regions (DMRs) involved in many important biological events, including genomic imprinting and diseases. Thus, the unique ability of TALE to read epigenetic markers makes it possible for the epigenetic genome-dependent application of TALEs in vivo in future.

As used herein, the term "polynucleotide" refers to a deoxyribonucleotide or ribonucleotide polymer with a linear or circular conformation and in a single- or double-stranded form.

As used herein, the terms "polypeptide", "peptide", and "protein" are used interchangeably to refer to a polymer of amino acids in which one or more amino acids may be naturally occurring amino acids, or chemical analogs or modified derivatives thereof.

As used herein, "binding" refers to sequence-specific, non-covalent interactions between macromolecules (e.g., between a protein and a nucleic acid). As used herein, the term "binding polypeptide" is a polypeptide or protein which can bind to another molecule non-covalently, wherein another molecule can be a DNA molecule, an RNA molecule and/or a protein molecule.

As used herein, the term "TALEs" refers to transcription activator-like effectors that specifically recognizes a DNA sequence, and it comprises a DNA binding domain (also referred to as TALE repeats domain or TALE repeats) and the flanking N-terminal and C-terminal non-repeat sequences. The DNA binding domain consists of tandem "repeats". Each "repeat" comprises 33-35 amino acids, in which residues 12 and 13 are key positions for targeted recognition and are referred to as repeat-variable residues (RVDs), each RVD recognizes only one base. TALEs or a DNA binding domain thereof recognizes the DNA target sequence corresponding to the RVD in sequence by RVD.

A naturally occurring TALEs generally contains 1.5-33.5 repeats, but studies have shown that at least 6.5 repeats are generally required for efficient recognition and binding of DNA, while 10.5 or more repeats exhibit greater activity (Boch, Jens, and Ulla Bonas. "Xanthomonas AvrBs3 family-type III effectors: discovery and function." Annual review of phytopathology 48 (2010): 419-436.; Boch, Jens, et al. "Breaking the code of DNA binding specificity of TAL-type III effectors." Science 326.5959 (2009): 1509-1512.)

The TALE repeat may be a truncated repeat, also referred to as a half-repeat, i.e. it is part of the N-terminus of the complete repeat, and the truncated repeat comprises the RVD. Typically, the final repeat at the carboxy terminus of the natural TALE repeats domain is a truncated repeat. Half-repeat typically comprises 17-20 amino acids.

In the present invention, in some embodiments, the number of the repeats of TALEs can be 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35. The repeats of TALEs may comprise 6, 7, 8, 9, 10, 11, 12, 13, 14, 15, 16, 17, 18, 19, 20, 21, 22, 23, 24, 25, 26, 27, 28, 29, 30, 31, 32, 33, or 34 complete repeats and one half-repeat.

In a preferable embodiment, the TALEs comprises 14 complete repeats and 1 half-repeat, wherein the half-repeat is located at the carboxyl terminus of the complete TALE repeats.

In a preferable embodiment, the single "repeat" in TALEs may be LTPEQVVAIASXX'GGKQALETV QRLLPV LCQAHG (SEQ ID NO. 1). In some embodiments, the half-repeat sequence in a TALE is LTPEQVVAIASXX'GGKQ (SEQ ID NO. 2). Wherein XX' is RVD.

The TALE repeats sequence used in the examples of the present invention is the amino acid sequence of an AvrBs3 protein in Xanthomonas. In addition to this sequence, the RVDs in the present invention are also applicable to TALEs containing a sequence of other repeats. AvrBs3 has different homologues in different subspecies of Xanthomonas, and the specific sequences of these homologues can be found in the following article: Boch, Jens, and Ulla Bonas. "Xanthomo-nas AvrBs3 family-type III effectors: discovery and function. "Annual review of phytopathology 48 (2010): 419-436.

In the present invention, the amino acids in a polypeptide sequence are shown by one-letter abbreviations, and the amino acids involved in the present invention and their one-letter abbreviations are as follows:

| Glycine | Gly | G |
| Alanine | Ala | A |
| Valine | Val | V |
| Leucine | Leu | L |
| Isoleucine | Ile | I |
| Proline | Pro | P |
| Phenylalanine | Phe | F |
| Tyrosine | Tyr | Y |
| Tryptophan | Trp | W |
| Serine | Ser | S |
| Threonine | Thr | T |
| Cystine | Cys | C |
| Methionine | Met | M |
| Asparagine | Asn | N |
| Glutamine | Gln | Q |
| Aspartic acid | Asp | D |
| Glutamic acid | Glu | E |
| Lysine | Lys | K |
| Arginine | Arg | R |
| Histidine | His | H |

In the present invention, when describing RVD, * indicates the deletion of an amino acid at this position.

As used herein, "base" and "nucleotide" are used interchangeably and refer to a compound consisting of a purine or pyrimidine base, a ribose or deoxyribose, and a phosphate, and they are the major constituents of DNA and RNA sequences. Common deoxynucleotides include cytosine (C), thymine (T), adenine (A), and guanine (G).

In addition to the four canonical deoxyribonucleotides described above, the mammalian genome contains modified DNA bases. For example, 5-methylcytosine (5mC), known as the fifth DNA base, is an important epigenetic marker for regulating gene expression. 5mC can be oxidized successively by 10-11 translocatase (TET) family proteins to produce 5-hydroxymethylcytosine (5hmC), 5-formylcytosine (5fC) and 5-carboxycytosine (5caC). In addition to the methylation on cytosine, another common DNA methylation, N6-methyladenine (6 mA), plays an important role in prokaryotic cells as a covalent modification on adenine of DNA.

As used herein, a "methylated base" refers to a base having a methylation, including 5-methylcytosine (5mC), 5-hydroxymethylcytosine (5hmC), and 6-methyladenine (6 mA).

RVDs with specific recognition abilities to 5mC, 5hmC or 6 mA, and degenerate RVDs capable of recognizing these methylated bases and the corresponding unmodified bases are found in the present invention, and the details are shown in the following table:

| Bases to be recognized | RVDs |
|---|---|
| 5mC | HA, NA |
| 5hmC | FS |
| C, 5mC | N*, NG, KP |
| C, 5hmC | HV, KV |
| 5mC, 5hmC | K*, RG |
| C, 5mC, 5hmC | G*, H*, R*, Y* |
| 6Ma | NP, FT, CV, CP |
| 6mA, A | RI, NI, KI, HI |

According to the table above, RVD HA or NA can specifically recognize 5mC, i.e., 5mC can be distinguished from 5hmC and C; RVD FS can specifically recognize 5hmC, i.e., 5hmC can be distinguished from 5mC and C; RVD NP, FT, CV or CP can specifically recognize 6 mA, i.e., 6 mA can be distinguished from A; degenerate RVD N*, NG or KP can recognize both C and 5mC.

Unless otherwise specified in the context of in the present invention, when abase recognized by RVD is described, "C" refers to a cytosine without methylation; "A" refers to an adenine without methylation; "5mC" refers to 5-methylcytosine; "5hmC" refers to 5-hydroxymethylcytosine; and "6 mA" refers to 6-methyladenine.

According to the present invention, the "specific recognition" of a particular methylated base means that the binding affinity of the RVD for that particular methylated base is significantly stronger than that for the same base with other forms of modification, the same base without modification, or other different bases.

Binding affinity can be determined by a variety of methods well known to those skilled in the art, for example, by referring to the descriptions of the references listed below, constructing a TALE-VP64-mCherry construct, and reporter DNA fragments comprising different modified bases and fluorescent protein genes, and then using the increased folds of the fluorescent protein signal resulted from binding and activating the reporter DNA fragments by the TALE-VP64 protein expressed from the TALE-VP64-mCherry construct in the cells, to determine the binding affinities of the RVD in TALEs and the different modified bases in the reporter DNA fragments. When the EGFP fold induction of an RVD for a specifically modified base is significantly higher than that of other forms of bases, it can be considered that the RVD can specifically recognize the specific modified base. Binding affinity can also be determined by an in vitro protection assay as described in Example 4 of the present invention.

According to the table above, the present invention has found that RVD HA or NA can specifically recognize 5mC. The binding affinity of RVD HA or NA for 5mC is significantly stronger than that for 5hmC and C. With the RVD, 5mC can be distinguished from 5hmC and C, and then the specific binding of TALE to 5mC and various specific applications depending on 5mC can be achieved.

Various applications depending on 5mC include, but are not limited to, the detection of 5mC in a gene, 5mC-dependent gene expression regulation, genome editing, epigenetic modification etc. (i.e., gene expression regulation, genome editing, or epigenetic modification is not performed in the presence of 5mC in the target sequence; while gene expression regulation, genome editing, or epigenetic modification is performed in the presence of C or 5hmC at the corresponding position), 5mC-dependent chromosome labeling in living cells (i.e., only the gene with 5mC at the corresponding position in the chromosome is labeled, and those with C or 5hmC at the corresponding position are not labeled; thus methylation of cytosine in the gene can be observed in living cells), and the proteins binding to 5mC containing sequences can be prepared.

The present invention also finds that RVD FS specifically recognizes 5hmC. The binding affinity of RVD FS for 5hmC is significantly stronger than that for 5mC and C, with the RVD, 5hmC can be distinguished from 5mC and C, and then specific binding of TALE to 5hmC and various specific applications depending on 5hmC can be achieved.

Various applications depending on 5hmC include, but are not limited to, the detection of 5hmC in a gene, 5hmC-dependent gene expression regulation, genome editing, epigenetic modification (i.e., gene expression regulation, genome editing, or epigenetic modification is not performed in the presence of 5hmC in the target sequence; while gene expression regulation, genome editing, or epigenetic modification is performed in the presence of C or 5mC at the corresponding position), 5hmC-dependent chromosome labeling in living cells (i.e. only the gene with 5hmC at the corresponding position in the chromosome is labeled, and those with C or 5mC at the corresponding position are not labeled; thus the methylation of hydroxycytosine in the gene can be observed in living cells), and the proteins binding to 5hmC containing sequences can be prepared.

The present invention also finds that RVD NP, FT, CV or CP specifically recognizes 6 mA. The binding affinity of these RVDs for 6 mA is significantly stronger than that for A, with the RVDs, 6 mA can be distinguished from A, and then the specific binding of TALE to 6 mA and various specific applications depending on 6 mA can be achieved.

Various applications depending on 6 mA include, but are not limited to, the detection of 6 mA in a gene, 6 mA-dependent gene expression regulation, genome editing, epigenetic modification (i.e., gene expression regulation, genome editing, or epigenetic modification is not performed in the presence of 6 mA in the target sequence; while gene expression regulation, genome editing, or epigenetic modification is performed in the presence of A at the corresponding position), 6 mA-dependent chromosome labeling in living cells (i.e. only the gene with 6 mA at the corresponding position in the chromosome is labeled, and those with A at the corresponding position are not labeled; thus the methylation of adenine in the gene can be observed in living cells), and the proteins binding to 6 mA containing sequences can be prepared.

The present invention also finds that the degenerate RVD N*, NG, or KP can recognize C and 5mC. These degenerate RVDs bind to C and 5mC with similar binding affinities, and the binding affinities of these degenerate RVDs for C and 5mC are significantly stronger than that for 5hmC.

The present invention also finds that the degenerate RVD HV or KV can recognize C and 5hmC. These degenerate RVDs bind to C and 5hmC with similar binding affinities, and the binding affinities of these degenerate RVDs for C and 5hmC are significantly stronger than that for 5mC.

The present invention also finds that the degenerate RVD K* or RG can recognize 5mC and 5hmC. These degenerate RVDs bind with similar binding affinities to 5mC and 5hmC, and the binding affinities of these degenerate RVDs to 5mC and 5hmC are significantly stronger than that for 5mC.

The present invention also finds that the degenerate RVD G*, H*, R*, or Y* can recognize C, 5mC, and 5hmC. These degenerate RVDs bind to C, 5mC and 5hmC with similar affinities.

The present invention also finds that degenerate RVD RI, NI, KI or HI can recognize 6 mA and A. These degenerate RVDs bind to A and 6 mA with similar binding affinities.

The degenerate RVDs can recognize two or three different methylated or unmethylated bases at the same time, and can be used under the condition that the methylation of the bases is not known, to improve the target binding efficiency of TALEs, and to reduce the influence of methylation on the binding of TALEs to a target sequence. For example, 5mC in the cell genome can be oxidized to 5hmC by the catalysis of a TET family protein, and the use of a degenerate RVD capable of simultaneously recognizing 5mC and 5hmC can avoid the reduction of the binding efficiency caused by different kinds of cytosine methylations. Therefore, according to different experimental purposes in specific experiments, the RVD capable of specifically identifying a specific methylated base, the degenerate RVD capable of identifying two methylated bases, and the degenerate RVD capable of identifying three methylated bases can be combined to meet the specific experimental requirements.

The RVDs of the present invention can be used in any application where a binding to a particular methylated base is needed, either in vitro or in vivo, and these applications may be non-therapeutic.

The TALEs containing an RVD of the present invention may be expressed as a DNA binding polypeptide for binding a base with a particular methylation. In some cases, such DNA binding polypeptides may function as "antibodies" to bind their "antigens" (i.e., target sequences containing bases with particular methylations). In some cases, such DNA binding polypeptides may bind a target sequence containing a base with a particular methylation, thereby protecting it from nuclease cleavage or interaction with other DNA binding polypeptides (e.g., transcription regulators, etc.).

The TALEs containing an RVD of the present invention can also be coupled with a fluorescent protein to form a fusion protein, which can bind to a target sequence containing a specific methylated base on a chromosome in a living cell, thereby the dynamic change of the chromosome can be observed in the living cell.

Fluorescent proteins are well known to those skilled in the art, and include but are not limited to, green fluorescent proteins (GFPs), enhanced green fluorescent proteins (EGFPs), red fluorescent proteins (RFPs), or blue fluorescent proteins (BFPs), etc.

The TALEs containing an RVD of the present invention can also be coupled to a functional domain to form a fusion protein, with said protein the manipulation of a gene of interest containing a specific methylated base can be achieved. Said manipulation may be genome editing, regulation of gene expression, or epigenetic modification, etc., and the functional domain may be a functional domain for genome editing, a domain for regulating gene expression, or a domain for epigenetic modification.

The term "genome editing" refers to altering a gene sequence at a target site, including insertion, deletion or substitution of a gene. For example, the genome editing may be the double-stranded DNA cleavage at a target site, the formation of DNA single-stranded gaps, and the like by using nucleases, followed by insertion and deletion (indel) of DNA during non-homologous end ligation (NHEJ) repair of a DNA sequence, resulting in frame shift mutations, thereby achieving gene knockout. A functional domain for genome editing refers to an amino acid sequence capable of achieving a genome editing function.

When genome editing is performed by using a fusion protein comprising TALEs with RVDs of the present invention and a functional domain for genome editing, wherein the functional domain for genome editing may be a nuclease. Nucleases include, but are not limited to, endonucleases, zinc finger nucleases (ZFN), Cas9 nucleases. The application of Cas9 nuclease is well known to those skilled in the art, and is generally used by co-introducing Cas9 nucleases and sgRNA into a cell to perform the cleavage of a target sequence.

In the present invention, when genome editing is performed, it is preferable that the fusion protein be provided in the form of TALEN, wherein the functional domain for genome editing is the DNA cleavage domain of FokI endonuclease.

The term "regulation of gene expression" refers to altering the expression of a gene or the level of an RNA molecule, including non-coding RNAs and RNAs encoding one or more proteins or protein subunits. "regulation of gene expression" also includes altering the activity of one or more gene products, proteins, or protein subunits. A functional domain for regulating gene expression refers to an amino acid sequence capable of regulating expression of a target gene.

The functional domain regulating gene expression may be a transcriptional activator or a functional fragment thereof, or a transcriptional repressor or a functional fragment thereof.

The term "epigenetic modification" refers to modifications of DNA, including methylation of DNA, DNA demethylation, and the like, without altering the DNA sequence of a gene of interest. A functional domain for epigenetic modification refers to an amino acid sequence capable of performing the epigenetic modification of a gene of interest.

The functional domains for epigenetic modification may be methyltransferases or demethylases.

The term "functional fragment" means it has the sequence of a part of a full-length protein or polypeptide, and yet has the same function as the full-length protein or polypeptide, for example, a protein domain capable of performing the corresponding function under specific experimental conditions, such as a cleavage domain of a nuclease.

The cells described herein can be any cell or cell line of a plant, animal (e.g., a mammal such as a mouse, rat, primate, livestock, rabbit, etc.), fish, etc., and can also be a eukaryotic cell (e.g., a cell of yeast, plant, fungus, fish, and mammalian such as cat, dog, mouse, cattle, sheep, and pig).

The cells described herein can be oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells, and HeLa cells, HEK293T cells, etc.

The methods of any of the embodiments according to the invention can be performed in vitro or in vivo.

The methods of any of the embodiments according to the invention may be non-therapeutic.

Example 1 Materials and Methods

1. DNA Synthesis and Purification

Oligo DNA primers were synthesized on an Expedite 8909 DNA/RNA synthesizer by using standard reagents including 5mC and 5hmC phosphoramidites (Glen Research). Oligo DNA was deprotected by standard methods recommended by Glen Research Corp. and purified by Glen-Pak DNA purification cartridge.

The synthesized DNA was verified by high-performance liquid chromatograph (HPLC), briefly: DNA was digested into nucleosides with nuclease P1 (Sigma, N8630) and alkaline phosphatase (Sigma, P4252). The nucleosides were separated on SB-Aq C18 column (Agilent) by using 5% to 50% Acetonitrile in 30 min.

2. Cell Culturing, Transfection and Flow Cytometric Analysis

HEK293T cells (from Stanley Cohen lab at Stanford University) and Hela cells (preserved in our lab) were cultured in DMEM with 10% FBS and 1% penicillin-streptomycin at 37° C. and 5% $CO_2$. Cells were seeded in 24-well plates 24 h prior to transfection at a density of $7 \times 10^4$ cells per well. The cells in each well were co-transfected with 0.15 μg of TALE-(XX')$_3$ plasmid and 0.15 μg of reporter DNA by using polyethylenimine (PEI). At 48 h post-transfection, cells were collected and analyzed on BD LSR Fortessa flow cytometer (BD Biosciences). EGFP and mCherry protein expression was quantified respectively by using lasers with wavelengths of 488 and 561 nm. At least 10,000 events were collected from each sample to obtain sufficient data for analysis. Cells with mCherry fluorescence intensity of $5\times10^3$-$5\times10^4$ were gated for analysis.

3. Construction of TALEN

TALEN plasmid backbone contains a CMV promoter, a nuclear localization signal, TALEs amino- and carboxyl-terminal non-repeat sequences, and a FokI endonuclease monomer, the specific sequences are described in the reference 37 below.

In use, TALE repeats containing different RVDs are inserted into a TALEN backbone vector to verify the effects of different RVDs, and the construction method thereof is described in Yang, Junjiao, et al. "Assembly of Customized TAL Effectors Through Advanced ULtiMATE System." *TALENs: Methods and Protocols* (2016): 49-60.

4. Expression and Purification of TALE Proteins

The expressed and purified TALE proteins were used for in vitro protection assays.

TALE repeats with canonical RVDs (i.e., NI, NG, HD, and NN) were constructed by using the ULtiMATE system, as previously described (37). For using TALE repeats containing new RVDs, monomer of said units were synthesized separately. The final assembly of these TALEs constructs was performed by using the same ULtiMATE protocol as previously described (37).

TALE repeats were constructed into TALEN backbone to construct a TALEs expression plasmid. And a fragment containing the N- and C-terminal sequences of TALEs with internal repeats was amplified from the corresponding TALEN plasmid and cloned into NheI and HindIII sites of pET-28a (+).

The sequence of TALEs (containing His tag for purification, N- and C-terminal sequence of TALEs and TALE repeats which specifically recognizes DNA) with different RVDs was cloned into a pET-28a vector (Novagen). Overexpression of TALEs was induced in *E. coli* BL21 (DE3) by 1.0 mM isopropyl β-D-thiogalactoside (IPTG) when the cell density reached an OD600 of 0.8. After growth at 20° C. for 16 h, the cells were harvested, and re-suspended in the buffer containing 25 mM Tris-HCl, pH 8.0, and 150 mM NaCl, disrupting by using sonication. The recombinant proteins were purified sequentially through $Ni^{2+}$-nitrilotriacetate affinity resin (Ni-NTA, GE healthcare) (Buffer A: 10 mM Tris-HCl, pH 8.0, 300 mM NaCl, and Buffer B: 10 mM Tris-HCl, pH 8.0, 300 mM NaCl, and 500 mM imidazole), and HiLoad superdax PG200 (GEHealthcare) (Buffer GF: 10 mM Tris-HCl, pH 8.0, 100 mM NaCl).

5. TALE Repeats

The TALE repeats used in the following examples comprise 14 consecutive repeats and a half repeat, wherein each repeat comprises 34 amino acid residues, the sequence of the unit is: LTPEQVVAIASXX'GGKQALETVQRLLPV-LCQAHG (SEQ ID NO. 1), and the half repeat comprises the first 17 amino acid residues of a single repeat, the sequence of the half repeat is: LTPEQVVAIASXX'GGKQ (SEQ ID NO. 2). Wherein XX' refers to an RVD.

The materials and methods described in this Example were applied in Examples 2-7 below.

Example 2 Construction of Artificial Screening System

The artificial screening system consists of reporter DNA elements and a TALE-VP64 expression library.

Figure 1:
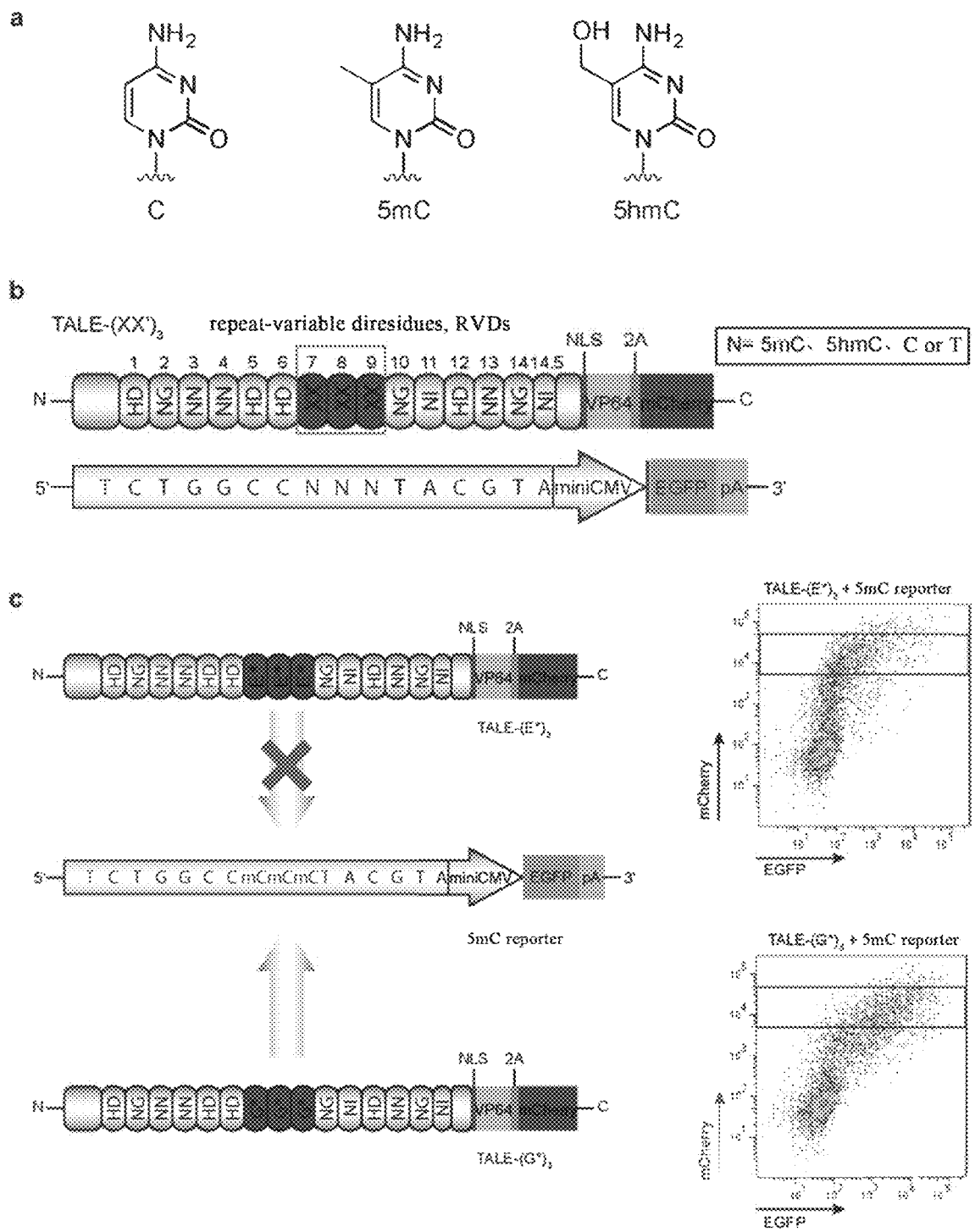
FIG. 1 is a schematic for evaluation of screening all potential TALE RVDs recognizing modified cytosines. (a) Chemical structures of C, 5mC, and 5hmC. (b) A schematic of a system for screening a novel RVD for modified cytosine, and it is composed of TALEs activator and a GFP expression reporter DNA fragment. (c) When the customized TALEs do not bind to the reporter DNA fragment (left panel), for instance, TALE-(E*)$_3$ versus the reporter DNA fragment comprising 5mC, the GFP expression is at a basal level (right panel). In contrast, when the TALEs bind tightly to the reporter DNA fragment (left panel), for instance, TALE-(G*)$_3$ versus the reporter DNA fragment containing 5mC, the GFP expression is up-regulated (right panel). The mCherry intensity indicates the transfection efficiency of the TALE-(XX')$_3$ plasmid.

The TALE-VP64 expression library includes 400 TALE-VP64-mCherry constructs, each of the constructs is a circular plasmid expressing the TALE-VP64 fusion protein when it is transfected into a cell (see reference 37 below for details). As shown in FIG. 1B, each construct contains an artificial TALEs array including 14.5 repeats fused to VP64, for repeats 1-6, 10-14 and the last half repeat (the repeat 14.5 is shown in FIG. 1B) they are identical between the different constructs, while for repeats 7-9 they are different between the different constructs. For each construct, the artificial TALEs array containing three consecutive RVD monomers on the 7th to 9th repeats are referred to as TALE-(XX')$_3$, wherein the three consecutive RVD monomers are encoded by the same six randomly synthesized nucleotides, i.e., the 7th to 9th tandem repeats express three identical RVDs, thereby forming 400 TALEs with different test RVDs XX', so as to detect the recognition of 5mC and 5hmC by different RVDs. Wherein X and X' represent the 12th and 13th residue (i.e. RVD) respectively in the repeat. In addition, since N* was previously found to recognize 5mC, an additional 20 TALE-(X*)$_3$ with absence of residue 13 were assembled. Hereinafter, TALE-(XX')$_3$ and TALE-(X*)$_3$ described above are collectively referred to as TALE-(XX')$_3$. Accordingly, the TALE-VP64 expression library used comprises a total of 420 TALE-VP64-mCherry constructs respectively containing 420 different TALE-(XX')$_3$. Hereinafter, the 420 TALE-VP64-mCherry constructs are collectively referred to as TALEs constructs, also as TALE-(XX')$_3$ plasmids or TALE-(XX')$_3$ expression plasmids.

A TALE-VP64 expression library was generated. Specifically, 420 TALE-(XX')$_3$ are divided into two groups, wherein the amino acid residues 12 and 13 of the RVD of the 7th to 9th repeats of the 400 TALE-(XX')$_3$ plasmids are a combination of 20 natural amino acid residues, and the construction method of such TALE-(XX')$_3$ plasmids is as described in the reference 13 below.

The RVDs expressed by the 7th to 9th repeats of the other 20 TALE-(XX')$_3$ are RVDs in which the amino acid residue 13 was deleted, i.e. A*, C*, D*, E*, F*, G*, H*, I*, K*, L*, M*, N*, P*, Q*, R*, S*, T*, V*, W*, Y*. These 20 TALE-(XX')$_3$ expression plasmids were constructed respectively as described in the reference 13 below. That is, a forward primer 5'-tCGTCTCaGAACAGGTTGTAGCCAT-AGCTTCTNNNNNNGGAGGTAAGCAGGCACTGGAA-3' (SEQ ID NO: 3; NNNNNN represents the sequence encoding a particular RVD) encoding a particular RVD, and an identical reverse primer 5'-aaCGTCTCAGTTCGGGT-CAACCCATGAGCCTGACACAAGTACTGGGAGCA-GGCGCTGCA CGGGTTTCCAGGTGCCTGCTT-3' (SEQ ID NO: 4) are used to generate a 102 bp fragment containing BsmBI restriction endonuclease sites at both terminals by annealing and PCR extension. Thereafter, the TALE monomer fragments were ligated together by 6 Golden-Gate cleavage-ligation cycles, and the TALE multimers were amplified by using primers G-lib-F and G-lib-R. And finally, the fragments containing only three TALE monomers are collected through gel extraction, ligated to a library expression vector constructed in advance, and transfected to Trans1-T1 competent cells. The correct TALE-(XX')$_3$ plasmids expressing the corresponding RVDs were obtained by Sanger sequencing. Wherein:

G-lib-F:
(SEQ ID NO: 5)
5'-TAGCTATACGTCTCATTGACCCCCGAACAGGTTGTAGCC-3'

G-lib-R:
(SEQ ID NO: 6)
5'-TAGCTATACGTCTCACCCATGAGCCTGACACAGTACTGGGAGCA-3'.

A reporter DNA element is a linear DNA fragment containing a TALE-(XX')₃ recognition sequence, a miniCMV promoter, an EGFP protein encoding sequence and a polyA signal (FIG. 1b). The TALE-(XX')₃ recognition sequence in a reporter DNA element has 15 bases in length, wherein the bases 1-6, 10-15 are recognized by the RVDs contained in the repeats 1-6, 10-14.5 of the library of TALEs constructs, respectively. The 7th to 9th bases of the TALE-(XX')₃ recognition sequence in the reporter DNA elements may be three consecutive 5mC, 5hmC or 6 mA for detecting the binding capacity of different RVDs to the corresponding methylated bases, and said recognition sequences are referred to as 5mC reporter DNA element, 5hmC reporter DNA element, or 6 mA reporter DNA element, respectively. One or more of the reporter DNA elements are determined to be used according to the methylated bases to be screened. Reporter DNA elements, approximately 1450 bp in size, were obtained from PCR amplification with chemically synthesized forward primers Report-F containing a specific methylated base and identical reverse primers Report-R.

The primer sequences are as follows:

Report-F:
(SEQ ID NO: 7)
5'-G*C*C*AGATATACGCGTTACTGGAGCCATCTGGCCNNNTACGTAGGCG
TGTAC-3', wherein N represents 5mC, 5hmC or 6mA;

Report-R:
(SEQ ID NO: 8)
5'-A*G*C*GTCTCCCGTAAAGCACTAAATCGGAACCCTAAAGGGAGC-3'
(*indicates a thio-modified base, the major
function of which is to protect the reporter DNA
element from degradation by nucleases in the
cells; the underline indicates TALE-(XX')₃
recognition sequence, i.e., the TALEs binding
sequence)

Figure 2:
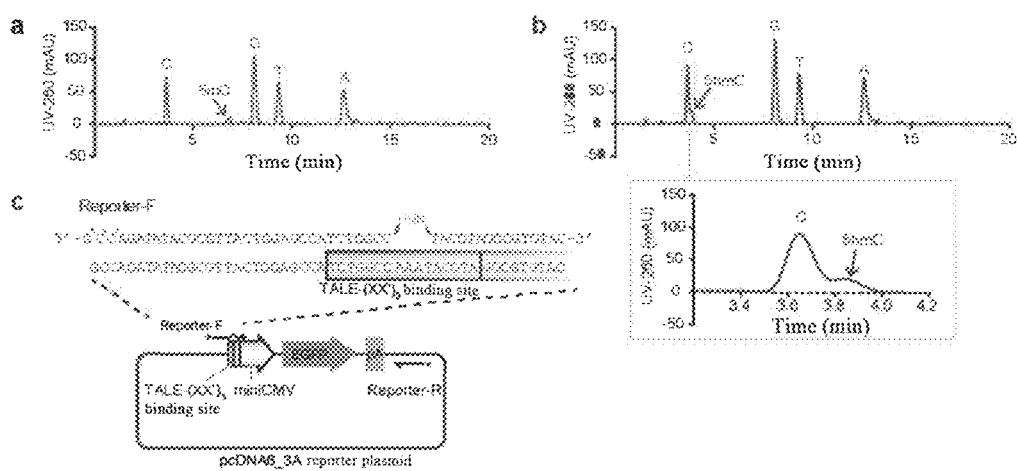
FIG. 2 shows the preparation of a reporter DNA fragment containing 5mC and 5hmC. 5mC and 5hmC are incorporated into the primer used for generating a reporter DNA fragment containing 5mC and 5hmC. The HPLC chromatographs show the incorporation of 5mC (a) and 5hmC (b); in the zoom-in picture, the 5hmC peak can be clearly observed. (c) a schematic of PCR amplification for a reporter DNA fragment containing 5mC and 5hmC.

The construction process of the reporter DNA elements are as follows. Firstly, the reporter plasmid pcDNA6_3A (FIG. 2c) is amplified from E. coli, said plasmid contains the template sequence CTGGCCAAATACGTA (SEQ ID NO: 9) of TALE-(XX')₃ binding site; then the primers described above containing 5mC, 5hmC or 6 mA are synthesized chemically, and the linear reporter DNA elements containing 5mC, 5hmC or 6 mA in the TALEs binding sequence are generated by PCR (FIG. 2c). The forward primer contains CTGGCCNNNTACGTA (SEQ ID NO: 10), the binding sequence of TALE-(XX')₃, and is located immediately upstream of the minimal CMV promoter (pminiCMV) and its downstream EGFP gene, wherein N represents 5mC, 5hmC or 6 mA. And wherein the bases corresponding to the 7th-9th repeats of the TALEs binding sequence are 3 consecutive 5mC, 5hmC or 6 mA.

In addition, the manual screening system may also contain reporter DNA elements for C and T, said DNA elements are circular DNAs and constructed as described in the reference 13 below. The TALE-(XX')₃ recognition sequence contained in the system is the same as described above except that the NNN is CCC or TTT.

The specificity of TALE-(XX')₃ binding to the TALEs binding sequence in the reporter DNA elements is detected by measuring EGFP fluorescence levels through the manual screening system described above. Thus, a platform for systematic evaluation of TALE RVD recognition screening is constructed and obtained.

Example 3 Screening TALE RVDs for Recognition of Modified Cytosine

To measure the binding affinity of 420 RVDs for 5mC and 5hmC, each of the 420 TALEs constructs was introduced into HEK293T cells along with one of the three EGFP reporter DNA elements (containing three consecutive C, 5mC or 5hmC, respectively). The fluorescence levels of EGFP and mCherry were measured by using FACS analysis (FIG. 1c). The binding specificity of the 420 RVDs in TALEs constructs for C, 5mC and 5hmC respectively was determined by comparing fold changes in EGFP expression of each RVD relative to the baseline level of the corresponding base. The 1260 data points for C, 5mC and 5hmC, and the 420 data points for T in previous work (see the reference 13 below) are summarized in a heat map (FIGS. 3a and 4).

From the preliminary screening results of FIG. 3a, RVDs with higher binding affinities for 5mC and 5hmC were selected for validation experiments in triplicate. Those RVDs with EGFP fold induction of 4 or higher for 5mC or 5hmC reporter DNA fragments are assumed to be RVDs with stronger binding affinities for the two nucleotides, respectively. The results are shown in FIG. 3b.

As shown in the results, specific and degenerate RVDs efficiently recognizing 5mC and 5hmC were obtained from the screening. A plurality of binding agents with high binding affinities for 5mC are identified, and grouped into three categories based on the amino acid residue at position 13: RVDs containing Gly (NG, KG and RG), RVDs containing Ala (HA and NA), and RVDs containing deletions (N*, K*, H*, R*, Y* and G*). Among the RVDs containing Gly or deletions, there are universal RVDs (recognizing 5mC, 5hmC and canonical C) and degenerate RVDs (recognizing 5mC and 5hmC); and interestingly, two Ala-containing RVDs (HA and NA) are selective for 5mC. In previous studies, NG (natural binding agent of T) and N* were used to identify 5mC, while we also identified these two RVDs during the screening process, many new RVDs reported in our study have higher binding affinities for 5mC than that of said two RVDs. For example, HA, NA and X* (X refers to K, H, Y or G) are all verified to have stronger binding affinities for 5mC. Not surprisingly, the three RVDs were not found to bind canonical T, and they have either an amino acid residue with a small side chain or a deletion of the residue at position 13.

RVD selectively binding to 5hmC has not been reported previously. As noted above, we identified degenerate RVDs and universal RVDs that bind to 5hmC very well. Among them, ~15-fold induction was observed for these 5hmC binding agents, demonstrating their strong affinities for 5hmC. In addition, we observed a new set of 5hmC-binding RVDs with serine at residue 13 (FS, YS and WS). Although they have weaker affinities for 5hmC than universal binding RVDs, they preferentially bind to 5hmC rather than 5mC, providing the possibility of positive and selective 5hmC recognition. Taken together, we have found that the universal and degenerate binding agents of 5mC and 5hmC tend to have a glycine or a deletion at position 13, while the specifically binding agents of 5mC and 5hmC have an alanine or a serine at position 13, respectively.

Example 4 Quantitative Measurement of the Binding Affinity and Specificity of RVD for 5mC, 5hmC and Canonical C The recognition of DNA by the new RVD obtained in Example 3 was verified by an in vitro protection assay (the principle of the reaction is shown in FIG. 5a). In this assay, the sequence of MAPK6 gene, 5'-TTCAGCTGGAT[CCCGGGAGGA]GCGGATATAACCAGG-3' (SEQ ID NO: 11), was synthesized chemically. The TALEs recognition sequence designed for this sequence is shown in square brackets, and contains an MspI restriction endonuclease recognition site (underlined). DNA oligos that contain C, 5mC or 5hmC at a defined position (the position of the second C in the MspI recognition site) were synthesized chemically; endonuclease MspI was added to the DNA probes in the presence of varying concentrations of TALE proteins. The binding of TALE proteins to their cognate cytosine bases will inhibit DNA cleavage by the endonuclease, thereby resulting in a protected full-length band and a cleaved-DNA band during denaturing PAGE analysis. The protection efficiency is then calculated for each RVD, and is given in the form of inhibition constant (Ki, which is the measurement of the reciprocal of binding affinity). The inhibition constants of RVDs are obtained by getting the protection efficiency through the cleavage protection experiments of TALE proteins containing different RVDs with regard to C, 5mC and 5hmC, and then fitting the protection efficiency curves with GraphPad Prism 6 software and calculating the inhibition constants. The inhibition constants indicate the binding efficiencies of different RVDs for C, 5mC and 5hmC. The smaller inhibition constants indicate stronger protection efficiencies of RVDs and stronger binding to the corresponding DNA fragments.

In vitro protection assay was performed by using the endonuclease MspI (the principle of which is shown in FIG. 5a). Each 10 μL reaction system contains 1 nM labeled DNA, 1 μL of 10× CutSmart Buffer (NEB), and 100 nM NaCl. TALE proteins were added to a final concentration between 10 nM and 8 μM. The binding system was incubated at 25° C. for 30 min. Then 0.4 U of MspI was added, and the incubation was continued for 15 min. The reaction was quenched by adding 10 μL formamid, followed by heating at 95° C. for 5 min. Protected and cleaved DNA were separated by Urea-PAGE, and imaged by using Chemiluminescent Nucleic Acid Detection Module Kit (Thermo).

The assay was firstly optimized with RVD HD, and HD is a natural binder with high affinity for canonical cytosines. A low Ki of HD for C was observed, whereas the Ki of HD for either 5mC or 5hmC was at least 30-fold higher (FIGS. 5b and 5c, FIG. 6c), demonstrating the ability of the protection assay in quantitative assessment of binding affinity. In this in vitro assay, NG and N* were shown to bind to only 5mC rather than 5hmC (FIGS. 5b and 5c). Representative RVDs were selected from the screening results (FIG. 3b) for further evaluation. The 5mC-specific RVD HA showed a lowest Ki for 5mC, and its selectivity for 5mC is ~5 to 7 times higher than that for C and 5hmC in the in vitro assay. The 5hmC-specific RVD FS showed a ~5 to 6 times higher selectivity for 5hmC than that for C and 5mC, although its binding affinity for 5hmC did not appear as strong as that of HA for 5mC. In addition, the degenerate RVD RG showed comparable protection for 5mC and 5hmC, while universal RVD R*r combined with C, 5mC and 5hmC had similar affinities for all of the three. (See FIGS. 5b and 5c).

Example 5 New RVDs Activating Gene Expression in a Methylation-Dependent Manner To explore the potential of these new RVDs in recognizing cytosine methylation in vivo, we investigated their performance in targeted gene activation in human cells. A previously developed TALE-VP64 was used to design and construct a TALE-activator and achieve specific gene activation (37). The backbone of the TALEs-activator plasmid contains a CMV promoter, a nuclear localization signal, TALEs amino- and carboxyl-terminal non-repeat sequences, and an activator VP64, and the specific sequence of which is shown in the reference 37 below.

In use, TALE repeats containing different RVDs are inserted into the TALE-activator backbone to verify the effects of different RVDs. For the method of construction, see the article: Yang, Junjiao, et al. "Assembly of Customized TAL Effectors Through Advanced ULtiMATE System." *TALENs: Methods and Protocols* (2016): 49-60.

First the TET1 gene was selected by utilizing the existing methylation data from the USCS database, its promoter has a high methylation level in HeLa cells but is hypomethylated in HEK293T cells (FIG. 7a). A TALEs-activator with TALE repeats targeting to TET1 gene was constructed. In HeLa cells, all of the 5mC-specific HA, the degenerate RG, and the universal R* significantly activates TET1 expression (the standard of significant activation is to increase the expression of TET1 compared with the control group, and the expression of TET1 is significantly increased, *, $P<0.05$; **, $P<0.005$), with RG achieving about 10-fold induction (FIG. 7b). All of the three RVDs identified demonstrates better performance when they are compared with NG and N*. In addition, HD does not significantly upregulate TET1 expression. In HEK293T cells, HD binds well to the hypomethylated TET1 promoter and further enhances its expression (despite that its expression level is already high), HA and RG do not affect gene expression, while the affinity of universal R* for canonical C is weaker than that of HD, and it mildly upregulates gene expression. Since NG and N* can poorly discriminate unmodified C, they also slightly activated TET1 expression.

Then, TALEs-activators with TALE repeats targeting to LRP2 gene were constructed, and they target to the promoter region of the LRP2 gene, which is medium methylated in HeLa cells and hypomethylated in HEK293T cells (FIG. 7c). In addition, this region contains only two CpGs, and hence is more challenging for RVD-mediated discrimination.

HEK293T and HeLa cells were seeded in 6-well plates and grown to 60% confluence. For each well, 2 μg of TALEs-activator plasmid was transfected by using Lipofactamine® 2000 (Invitrogen). The transfected cells were cultured for 3 days, followed by sorting for mCherry-positive cells through flow cytometry. Total RNA was isolated from mCherry-positive cells and reverse transcribed. Real-time PCR analysis was performed on the ViiA™7 Real-Time PCR System (Applied Biosystems) at standard reaction condition by using SYBR Green 2× premix II (Takara).

It was observed that RVD (HA, RG) binding to 5 mC significantly activated genes in HeLa cells. In HEK293T cells, only HD and the universal RVD R*, but not the 5mC-binding RVDs, activated the expression of the LRP2 gene. Hence, the identified new RVDs (HA, RG) are capable of distinguishing medium methylated sites from unmethylated sites in vivo.

Example 6 Methylation-Dependent Genome Editing by Using New RVDs

To examine the possibility of methylation-dependent genome editing, we use TALEN constructs containing different RVDs (obtained by inserting TALE repeats into a TALEN expression vector). A TALEN expression vector (i.e., a TALEN plasmid backbone) contains a CMV promoter, a nuclear localization signal, TALEs amino- and carboxyl-terminal non-repeat sequences, and an endonuclease FokI monomer, and the specific sequence of which is described in the reference 37 below. The construction method refers to the article: Yang, Junjiao, et al. "Assembly of Customized TAL Effectors Through Advanced ULti-MATE System." TALENs: Methods and Protocols (2016): 49-60.) targeting the human PLXNB2 gene (FIG. 7e). The second exon of PLXNB2 that is highly methylated in HeLa cells (data from UCSC) was selected, and TALEN-mediated DNA cleavage was evaluated by using the indel rates (i.e., the ratio of insertion and deletion).

HeLa cells were seeded in 6-well plates and grown to 60% confluence. For each well, a pair of TALEN plasmids and pmaxGFP (Lonza Group Ltd.) were co-transfected at a ratio of 9:9:2 (0.9:0.9:0.2 μg) by using Xtreme Gene HP (Roche). The transfected cells were cultured for 3 days, followed by sorting for GFP-positive cells through flow cytometry. TALENs-targeting regions were PCR-amplified from the genome DNA of the isolated GFP positive cells. As previously described, TALEN-mediated indels were analyzed by mismatch-sensitive T7 endonuclease (T7E1; New England Biolabs) (41).

According to the result, the TALEN-HD shows negligible editing efficiency (FIG. 7f), suggesting that the presence of three 5mC modifications within this region efficiently blocks its binding. When the three HD-containing RVDs were replaced by 5mC-binding RVDs (HA, R*, NG and N* were tested), high indel rates were observed (FIG. 7f; and FIG. 8C). These results indicate that these RVDs enable the methylation-dependent genome editing in human cells.

Example 7 RVD-Mediated Detection of 5hmC in Mammalian Genome at Single Base Resolution The methylation ratio of cytosine can be determined by bisulfite sequencing; however, traditional bisulfite sequencing cannot distinguish 5hmC from 5mC (38). Indirect 5hmC detection by using C- and 5mC-binding TALE proteins was reported previously (32). To explore the possibility of direct 5hmC detection by using TALE proteins containing 5hmC-recognizing RVDs, we firstly synthesized model DNA sequences incorporated with 5hmC, 5mC and C at specific sites, and tested the selectivity of RVD FS for 5hmC detection. In an in vitro protection assay, the protected full-length DNAs were increased linearly as the ratio of 5hmC increased (FIG. 10). In contrast, when the ratio of 5mC and C was varied, the protection ratio showed very modest change. In the experiment, DNA fragments with identical sequences and containing either C, 5mC or 5hmC respectively were mixed at the ratios shown in the figures. The black circles indicate the change of protection degree as the ratio of 5hmC in the mixture of 5mC and 5hmC increased from 0% to 100%. The black triangles indicate the change of protection degree as the ratio of 5hmC in the mixture of C and 5hmC increased from 0% to 100%. The gray circles indicate the change of protection degree as the ratio of 5mC in the mixture of C and 5mC increased from 0% to 100%. As shown in FIG. 10, the protection degree of DNA by TALE-FS only increased slightly when the 5mC ratio in the mixture of C and 5mC increased. In comparison, as the ratio of 5hmC in the mixture of C and 5hmC and in the mixture of 5mC and 5hmC increased, the protection degree of DNA by TALE-FS also increased greatly, indicating that TALE-FS selectively protects DNA fragments containing 5hmC. These observations indicate that 5hmC-specific RVD FS can be used to detect 5hmC in genomic DNA samples with complex modifications (for nucleotides of interest, there are at least C, 5mC and 5hmC simultaneously).

FS-containing TALE proteins were used to perform locus-specific 5hmC detection in genomic DNA. Considering the complexity of the genomic DNA, CRISPR-cas9 system instead of restriction enzymes was used to generate DNA cleavage in this protection assay (FIG. 9a). A 10 bp sequence in the intron of mouse Slc9a9 gene was selected, and the first cytosine of said sequence was reported to be highly hydroxymethylated in mES cells (39).

The reaction conditions are as follows. Each 10 μL reaction system contains 50 ng of genomic DNA, 1 μL of 10×Cas9 nuclease reaction buffer (NEB) and 1 nM DTT. TALE proteins were added to a final concentration between 20 and 500 nM. The binding reaction was incubated at 25° C. for 30 min. A total of 5 μL preincubated Cas9 and sgRNA was added, and the incubation was continued at 37° C. for 1 h. The reaction was quenched by heating at 95° C. for 5 min. The DNA was purified by using Ampure Beads, and the qPCR was analyzed by using SYBR Green 2× premix II (Takara) on LightCycler® 96 (Roche).

The result shows that the protection efficiency of TALE-FS is much higher than that of TALE-HD (FIG. 9b), indicating that TALE-FS is capable of detecting one single 5hmC site in the complex environment of genomic DNA. To further explore the ability of this approach in 5hmC detection, we applied this method to the genomic DNA of additional cell lines whose hydroxymethylation level at the same site was unknown. Comparing to the mESC samples, the protection of genome DNA from these cells was much smaller when the concentration of TALE proteins (in RAW264.7, L-M(TK-) and L929 cells) is relative low (FIG. 9c), suggesting a lower level of 5hmC at this particular site in these cells. The results above show that TALE proteins containing the newly identified RVDs can be used to detect the hydroxymethylation status in genomic DNAs at base-resolution.

Example 8 Identification of 6 mA-Recognizing TALE RVD

The same screening system as described in Example 2 was used, i.e., the TALE-(XX')$_3$ library with independent RVDs and the linear DNA reporter system containing 6 mA, and they were co-transfected into HEK293T cells respectively, the EGFP expression fold induction of the 6 mA reporter system by TALE-(XX')$_3$ was detected through flow cytometry. FIG. 11 is a heat map showing the results of 6 mA screening with the 420 RVDs.

As shown in the heat map of 6 mA screening results, there are more TALE-(XX')$_3$ with activation effects for the 6 mA reporter system, and the first amino acids of them are either His (H), Lys (K), Asn (N) or Arg (R); while the second amino acids of these RVDs with high efficiency are mostly either Ile (I), Pro (P), Ser (S), Thr (T) or Val (V). According to the overlapped heat map (FIG. 11), among the above mentioned RVDs with relatively stronger recognition abilities for 6 mA, many of them also have good recognition abilities for unmodified adenines, such as the series RVDs of XI, XS, XT, XV, etc.; some of them are specific for 6 mA, such as the series RVDs of XP. FIG. 12 shows the experiment results of the selected RVDs capable of recognizing 6 mA on the basis of the preliminary screening results. In particular, triplicate confirmation experiments were performed by using some RVDs with an EGFP fold induction greater than 5 for the 6 mA reporter system.

Overall, the recognition ability and preference for 6 mA are also closely related to the second amino acids of RVDs. According to this study, XP RVDs and NA, CV, FT RVDs etc. shows obvious preference for 6 mA; while XI, XC and some of the XT series do not show obvious preference for the recognition of unmodified adenine and N6-methyladenine. The binding of Ile (I) to an A base is due to a van der Waals' interaction (45) between its side chain and the C8 and N7 of adenine, and therefore it may not be affected by the addition of methyl group at the 6th amino acid position. Among the RVDs with high specificities for 6 mA (6 mA/A>5), the background values for recognizing other unmethylated bases by FT, CV, CP and NP are lower (FIG. 13), wherein NP has the strongest recognition ability for 6 mA, and followed by FT, and then CV and CP, and they can be considered as the selected RVDs with the best preference for 6 mA.

In conclusion, the study shows that in general small amino acids (Gly and Ala) or deletion at the 13th position can increase the binding affinity for 5mC. This observation is consistent with previous findings that N* and NG (naturally recognizing T) can bind to 5mC. It is likely that the absence of bulky side chains at the 13th position may create enough space to accommodate the methyl group of 5mC. However, there are still exceptions to this general trend. For instance, it is observed that the binding affinity of HG for 5mC is very small, HG contains a smaller residue at the 13th position as compared with HD which is the natural binder of C. Interestingly, when the His at the 12th position is replaced by Arg (hence, changing into RG), we observed a strong binding to 5mC. As a matter of fact, RG also recognizes 5hmC. These observations indicate a potentially more complicated mode for recognizing modifications by the double residues. Crystal structures of these new RVDs in complexes formed with the modified cytosines are needed to fully understand the mechanism of recognizing modifications by TALEs.

The present application also demonstrates the TALE-mediated, methylation-dependent gene activation and genome editing for several hypermethylated genomic regions. As an important control, when the same regions are devoid of cytosine methylation (in different cells), gene activation almost cannot be observed. Hence, the new RVDs reported in this study may provide a possibility to manipulate target genes based on their modification status in vivo. It is known that many differentially methylated regions (DMR) are present, and they are involved in many important biological events, including genomic imprinting and diseases. Hence, the unique ability of TALE proteins to read out the epigenetic markers may enable future epigenome-dependent applications of TALE in vivo.

In addition, RVDs (such as CV, FT, NP etc.) with relatively good preference for N6-methyladenine are found through high throughput screening in this study. These RVDs can be used for constructing sequence-specific N6-methyladenine binding TALE proteins to play a role similar to an antibody, and also can be used in combination with the RVDs which only recognize the unmodified A base so as to achieve the purpose of quantitative or qualitative detection of 6 mA. RVDs with unbiased preference for 6 mA and A bases, such as NI, can be used to unbiasedly target to sequences potentially containing methylated adenines, thereby overcoming the problem of inefficient genome editing caused by methylation modifications.

REFERENCES

1. Kay S & Bonas U (2009) How *Xanthomonas* type III effectors manipulate the host plant. Curr Opin Microbiol 12(1):37-43.
2. Kay S, Hahn S, Marois E, Hause G, & Bonas U (2007) A bacterial effector acts as a plant transcription factor and induces a cell size regulator. Science 318(5850):648-651.
3. Boch J & Bonas U (2010) *Xanthomonas* AvrBs3 family-type III effectors: discovery and function. Annu Rev Phytopathol 48:419-436.
4. Boch J, et al. (2009) Breaking the code of DNA binding specificity of TAL-type III effectors. Science 326(5959): 1509-1512.
5. Gurlebeck D, Thieme F, & Bonas U (2006) Type III effector proteins from the plant pathogen *Xanthomonas* and their role in the interaction with the host plant. J Plant Physiol 163(3):233-255.
6. Moscou M J & Bogdanove A J (2009) A simple cipher governs DNA recognition by TAL effectors. Science 326(5959):1501.
7. Bogdanove A J & Voytas D F (2011) TAL effectors: customizable proteins for DNA targeting. Science 333 (6051):1843-1846.
8. Morbitzer R, Romer P, Boch J, & Lahaye T (2010) Regulation of selected genome loci using de novo-engineered transcription activator-like effector (TALE)-type transcription factors. Proc Natl Acad Sci USA 107(50): 21617-21622.
9. Cong L, Zhou R, Kuo Y C, Cunniff M, & Zhang F (2012) Comprehensive interrogation of natural TALE DNA-binding modules and transcriptional repressor domains. Nat Commun 3:968.
10. Garg A, Lohmueller J J, Silver P A, & Armel T Z (2012) Engineering synthetic TAL effectors with orthogonal target sites. Nucleic Acids Res 40(15):7584-7595.
11. Christian M, et al. (2010) Targeting DNA double-strand breaks with TAL effector nucleases. Genetics 186(2):757-761.
12. Miller J C, et al. (2011) A TALE nuclease architecture for efficient genome editing. Nat Biotechnol 29(2):143-148.
13. Yang J, et al. (2014) Complete decoding of TAL effectors for DNA recognition. Cell research 24(5):628-631.
14. Miller J C, et al. (2015) Improved specificity of TALE-based genome editing using an expanded RVD repertoire. Nat Methods 12(5):465-471.
15. Kohli R M & Zhang Y (2013) TET enzymes, TDG and the dynamics of DNA demethylation. Nature 502(7472):472-479.
16. Pastor W A, Aravind L, & Rao A (2013) TETonic shift: biological roles of TET proteins in DNA demethylation and transcription. Nat Rev Mol Cell Biol 14(6):341-356.
17. Kriaucionis S & Heintz N (2009) The nuclear DNA base 5-hydroxymethylcytosine is present in Purkinje neurons and the brain. Science 324(5929):929-930.
18. Tahiliani M, et al. (2009) Conversion of 5-methylcytosine to 5-hydroxymethylcytosine in mammalian DNA by MLL partner TET1. Science 324(5929):930-935.
19. Ito S, et al. (2010) Role of Tet proteins in 5mC to 5hmC conversion, ES-cell self-renewal and inner cell mass specification. Nature 466(7310):1129-1133.

20. He Y F, et al. (2011) Tet-mediated formation of 5-carboxylcytosine and its excision by TDG in mammalian DNA. Science 333(6047):1303-1307.
21. Maiti A & Drohat A C (2011) Thymine DNA glycosylase can rapidly excise 5-formylcytosine and 5-carboxylcytosine: potential implications for active demethylation of CpG sites. J Biol Chem 286(41):35334-35338.
22. Pfaffeneder T, et al. (2011) The discovery of 5-formylcytosine in embryonic stem cell DNA. Angew Chem Int Ed Engl 50(31):7008-7012.
23. Huang Y & Rao A (2014) Connections between TET proteins and aberrant DNA modification in cancer. Trends Genet 30(10):464-474.
24. Bultmann S, et al. (2012) Targeted transcriptional activation of silent oct4 pluripotency gene by combining designer TALEs and inhibition of epigenetic modifiers. Nucleic Acids Res 40(12):5368-5377.
25. Valton J, et al. (2012) Overcoming transcription activator-like effector (TALE) DNA binding domain sensitivity to cytosine methylation. J Biol Chem 287(46):38427-38432.
26. Kim Y, et al. (2013) A library of TAL effector nucleases spanning the human genome. Nat Biotechnol 31(3):251-258.
27. Deng D, et al. (2012) Recognition of methylated DNA by TAL effectors. Cell research 22(10):1502-1504.
28. Dupuy A, et al. (2013) Targeted gene therapy of xeroderma pigmentosum cells using meganuclease and TALEN. PLoS One 8(11):e78678.
29. Hu J, et al. (2014) Direct activation of human and mouse Oct4 genes using engineered TALE and Cas9 transcription factors. Nucleic Acids Res 42(7):4375-4390.
30. Kubik G, Schmidt M J, Penner J E, & Summerer D (2014) Programmable and highly resolved in vitro detection of 5-methylcytosine by TALEs. Angew Chem Int Ed Engl 53(23):6002-6006.
31. Kubik G & Summerer D (2015) Achieving single-nucleotide resolution of 5-methylcytosine detection with TALEs. Chembiochem 16(2):228-231.
32. Kubik G, Batke S, & Summerer D (2015) Programmable sensors of 5-hydroxymethylcytosine. J Am Chem Soc 137(1):2-5.
33. Maurer S, Giess M, Koch O, & Summerer D (2016) Interrogating Key Positions of Size-Reduced TALE Repeats Reveals a Programmable Sensor of 5-Carboxylcytosine. ACS Chem Biol 11(12):3294-3299.
34. Rathi P, Maurer S, Kubik G, & Summerer D (2016) Isolation of Human Genomic DNA Sequences with Expanded Nucleobase Selectivity. J Am Chem Soc 138(31):9910-9918.
35. Deng D, et al. (2012) Structural basis for sequence-specific recognition of DNA by TAL effectors. Science 335(6069):720-723.
36. Mak A N, Bradley P, Cernadas R A, Bogdanove A J, & Stoddard B L (2012) The crystal structure of TAL effector PthXo1 bound to its DNA target. Science 335(6069):716-719.
37. Yang J, et al. (2013) ULtiMATE system for rapid assembly of customized TAL effectors. PLoS One 8(9): e75649.
38. Wu H & Zhang Y (2015) Charting oxidized methylcytosines at base resolution. Nat Struct Mol Biol 22(9):656-661.
39. Yu M, et al. (2012) Base-resolution analysis of 5-hydroxymethylcytosine in the mammalian genome. Cell 149(6):1368-1380.
40. Hsu P D, Lander E S, & Zhang F (2014) Development and applications of CRISPR-Cas9 for genome engineering. Cell 157(6):1262-1278.
41. Mussolino C, et al. (2011) A novel TALE nuclease scaffold enables high genome editing activity in combination with low toxicity. Nucleic Acids Res 39(21):9283-9293.
42. Fang, G., Munera, D., Friedman, D. I., Mandlik, A., Chao, M. C., Banerjee, O., Feng, Z., Losic, B., Mahajan, M. C., Jabado, O. J., et al. (2012). Genome-wide mapping of methylated adenine residues in pathogenic *Escherichia coli* using single-molecule real-time sequencing. Nature biotechnology 30, 1232-1239.
43. Fu, Y., Luo, G. Z., Chen, K., Deng, X., Yu, M., Han, D., Hao, Z., Liu, J., Lu, X., Dore, L. C., et al. (2015). N6-methyldeoxyadenosine marks active transcription start sites in *Chlamydomonas*. Cell 161, 879-892.
44. Greer, E. L., Blanco, M. A., Gu, L., Sendinc, E., Liu, J., Aristizabal-Corrales, D., Hsu, C. H., Aravind, L., He, C., and Shi, Y (2015). DNA Methylation on N6-Adenine in *C. elegans*. Cell 161, 868-878.
45. Koziol, M. J., Bradshaw, C. R., Allen, G. E., Costa, A. S., Frezza, C., and Gurdon, J. B. (2016). Identification of methylated deoxyadenosines in vertebrates reveals diversity in DNA modifications. Nature structural & molecular biology 23, 24-30.
46. Mak, A. N., Bradley, P., Cernadas, R. A., Bogdanove, A. J., and Stoddard, B. L. (2012). The crystal structure of TAL effector PthXo1 bound to its DNA target. Science 335, 716-719. Ratel, D., Ravanat, J. L., Berger, F., and Wion, D. (2006). N6-methyladenine: the other methylated base of DNA. BioEssays: news and reviews in molecular, cellular and developmental biology 28, 309-315.
47. Wion, D., and Casadesus, J. (2006). N6-methyl-adenine: an epigenetic signal for DNA-protein interactions. Nature reviews Microbiology 4, 183-192.
48. Zhang, G., Huang, H., Liu, D., Cheng, Y., Liu, X., Zhang, W., Yin, R., Zhang, D., Zhang, P., Liu, J., et al. (2015). N6-methyladenine DNA modification in *Drosophila*. Cell 161, 893-906.

The invention claimed is:

1. A method for detecting the presence of 5-methylcytosine (5mC) at a specific site of a target sequence in the genome of a cell, comprising:
   (1) introducing a protein comprising transcription activator-like effectors (TALEs) into the cell, wherein the TALEs target the target sequence, and in the TALEs the repeat variable diresidue (RVD) identifying the specific site is HA;
   (2) introducing a nuclease into the cell, wherein the targeted cleavage site of the nuclease is located in the TALEs target sequence; and
   (3) detecting whether the target sequence is cleaved, thereby judging whether 5mC is present at the specific site of the target sequence; if the target sequence is not cleaved, then the TALEs bind to the target sequence, and the nuclease does not bind to the target sequence and cleave it, thereby 5mC is present at the specific site; if the target sequence is cleaved, then the TALEs do not bind to the target sequence, and the nuclease binds to the target sequence and cleaves it, thereby 5mC is not present at the specific site.

2. The method of claim 1, wherein the nuclease is an endonuclease.

3. The method of claim 2, wherein the nuclease is a Cas9 nuclease.

4. The method of claim 3, wherein the Cas9 nuclease and an sgRNA are co-introduced into the cell in step (2).

* * * * *

SEQUENCE LISTING

```
<160> NUMBER OF SEQ ID NOS: 17

<210> SEQ ID NO 1
<211> LENGTH: 34
<212> TYPE: PRT
<213> ORGANISM: Artificial Sequence
<220> FEATURE:
<223> OTHER INFORMATION: artificially synthesized sequence
<220> FEATURE:
<221> NAME/KEY: misc_feature
<222> LOCATION: (12)..(13)
```

<223> OTHER INFORMATION: Xaa can be any naturally occurring amino acid

<400> SEQUENCE: 1

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 2
<211> LENGTH: 17
<212> TYPE: PRT
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: misc_feature
<222> LOCATION: (12)..(13)
<223> OTHER INFORMATION: Xaa can be any naturally occurring amino acid

<400> SEQUENCE: 2

Leu Thr Pro Glu Gln Val Val Ala Ile Ala Ser Xaa Xaa Gly Gly Lys
1               5                   10                  15

Gln

<210> SEQ ID NO 3
<211> LENGTH: 59
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: misc_feature
<222> LOCATION: (33)..(38)
<223> OTHER INFORMATION: n is a, c, g, or t

<400> SEQUENCE: 3
tcgtctcaga acaggttgta gccatagctt ctnnnnnngg aggtaagcag gcactggaa      59

<210> SEQ ID NO 4
<211> LENGTH: 80
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 4
aacgtctcag ttcgggtcaa cccatgagcc tgacacaagt actgggagca ggcgctgcac      60
gggtttccag gtgcctgctt                                                 80

<210> SEQ ID NO 5
<211> LENGTH: 39
<212> TYPE: DNA
<213> ORGANISM: Artificial Sequence
<220> FEATURE:
<223> OTHER INFORMATION: ARTIFICIALLY SYNTHESIZED SEQUENCE

<400> SEQUENCE: 5
tagctatacg tctcattgac ccccgaacag gttgtagcc                            39

<210> SEQ ID NO 6
<211> LENGTH: 44
<212> TYPE: DNA
<213> ORGANISM: Artificial Sequence
<220> FEATURE:

<223> OTHER INFORMATION: ARTIFICIALLY SYNTHESIZED SEQUENCE

<400> SEQUENCE: 6
tagctatacg tctcacccat gagcctgaca cagtactggg agca        44

<210> SEQ ID NO 7
<211> LENGTH: 51
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: modified_base
<222> LOCATION: (1)..(3)
<223> OTHER INFORMATION: thio-modified
<220> FEATURE:
<221> NAME/KEY: modified_base
<222> LOCATION: (34)..(36)
<223> OTHER INFORMATION: each base represents 5mC, 5hmC or 6mA
<220> FEATURE:
<221> NAME/KEY: misc_feature
<222> LOCATION: (34)..(36)
<223> OTHER INFORMATION: n represents A or C

<400> SEQUENCE: 7
gccagatata cgcgttactg gagccatctg gccnnntacg taggcgtgta c        51

<210> SEQ ID NO 8
<211> LENGTH: 42
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: modified_base
<222> LOCATION: (1)..(3)
<223> OTHER INFORMATION: thio-modified

<400> SEQUENCE: 8
agcgtctccc gtaaagcact aaatcggaac cctaaaggga gc        42

<210> SEQ ID NO 9
<211> LENGTH: 15
<212> TYPE: DNA
<213> ORGANISM: Artificial sequence
<220> FEATURE:
<223> OTHER INFORMATION: ARTIFICIALLY SYNTHESIZED SEQUENCE

<400> SEQUENCE: 9
ctggccaaat acgta        15

<210> SEQ ID NO 10
<211> LENGTH: 15
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: modified_base
<222> LOCATION: (7)..(9)
<223> OTHER INFORMATION: each base represents 5mC, 5hmC or 6mA.
<220> FEATURE:
<221> NAME/KEY: misc_feature
<222> LOCATION: (7)..(9)
<223> OTHER INFORMATION: n represents C or A

<400> SEQUENCE: 10
ctggccnnnt acgta        15

```
<210> SEQ ID NO 11
<211> LENGTH: 36
<212> TYPE: DNA
<213> ORGANISM: Artificial Sequence
<220> FEATURE:
<223> OTHER INFORMATION: ARTIFICIALLY SYNTHESIZED SEQUENCE
<220> FEATURE:
<221> NAME/KEY: protein_bind
<222> LOCATION: (12)..(21)
<223> OTHER INFORMATION: TALEs recognition sequence
<220> FEATURE:
<221> NAME/KEY: protein_bind
<222> LOCATION: (13)..(16)
<223> OTHER INFORMATION: MspI restriction endonuclease recognition site

<400> SEQUENCE: 11
ttcagctgga tcccgggagg agcggatata accagg                           36

<210> SEQ ID NO 12
<211> LENGTH: 16
<212> TYPE: DNA
<213> ORGANISM: Artificial Sequence
<220> FEATURE:
<223> OTHER INFORMATION: Artificially synthesized sequence
<220> FEATURE:
<221> NAME/KEY: modified_base
<222> LOCATION: (8)..(10)
<223> OTHER INFORMATION: each base is either 5mC or 5hmC
<220> FEATURE:
<221> NAME/KEY: misc_feature
<222> LOCATION: (8)..(10)
<223> OTHER INFORMATION: n represents C

<400> SEQUENCE: 12
tctggccnnn tacgta                                                 16

<210> SEQ ID NO 13
<211> LENGTH: 16
<212> TYPE: DNA
<213> ORGANISM: Artificial sequence
<220> FEATURE:
<223> OTHER INFORMATION: Artificially synthesized sequence
<220> FEATURE:
<221> NAME/KEY: modified_base
<222> LOCATION: (7)..(9)
<223> OTHER INFORMATION: m5c

<400> SEQUENCE: 13
tctggccccc tacgta                                                 16

<210> SEQ ID NO 14
<211> LENGTH: 10
<212> TYPE: DNA
<213> ORGANISM: Artificial sequence
<220> FEATURE:
<223> OTHER INFORMATION: Artificially synthesized sequence

<400> SEQUENCE: 14
tcccggagga                                                        10

<210> SEQ ID NO 15
<211> LENGTH: 17
<212> TYPE: DNA
<213> ORGANISM: Homo sapiens

<400> SEQUENCE: 15
taggcgtcct ccgcgac                                                17

<210> SEQ ID NO 16
```

```
<211> LENGTH: 17
<212> TYPE: DNA
<213> ORGANISM: Homo sapiens

<400> SEQUENCE: 16
tgcccgctgg attcccg                                                        17

<210> SEQ ID NO 17
<211> LENGTH: 48
<212> TYPE: DNA
<213> ORGANISM: Homo sapiens

<400> SEQUENCE: 17
tcgagtacgt gcctgacccc acctttgaga acttcacagg tggcgtca                      48
```